United States Patent [19]

Barker et al.

[11] 4,043,869

[45] Aug. 23, 1977

[54] WATER INSOLUBLE BIOLOGICALLY ACTIVE MATERIAL

[75] Inventors: Sidney Alan Barker; Charles John Gray, both of Birmingham, England

[73] Assignee: Koch-Light Laboratories, Ltd., England

[21] Appl. No.: 618,590

[22] Filed: Oct. 1, 1975

Related U.S. Application Data

[63] Continuation of Ser. No. 379,403, July 13, 1973, abandoned.

[30] Foreign Application Priority Data

July 13, 1972 United Kingdom ............... 32911/72

[51] Int. Cl.$^2$ ............................................. C07G 7/02
[52] U.S. Cl. ....................................... 195/63; 195/68; 195/DIG. 11; 260/112 R
[58] Field of Search .................... 195/63, 68, DIG. 11; 260/112 R

[56] References Cited

U.S. PATENT DOCUMENTS 3,167,485  1/1965  Katchalski et al. ............... 195/68 X
3,639,558  2/1972  Csizmas et al. ........................ 195/63

FOREIGN PATENT DOCUMENTS 1,136,039  12/1968  United Kingdom

OTHER PUBLICATIONS

Silman et al., Some Water–Insoluble Paper Derivatives Biopolymers, vol. 4, 1966 (pp. 441–448).
The Condensed Chemical Dictionary, 8th Ed., Van Nostrand Reinhold Co., N. Y. 1971, (pp. 10r and 68a).

*Primary Examiner*—David M. Naff
*Attorney, Agent, or Firm*—Allegretti, Newitt, Witcoff & McAndrews

[57] ABSTRACT

The invention relates to biologically active protein molecules, such as enzymes, attached to water-insoluble solids to render the molecules insoluble. In one aspect the attachment is effected by molecules of diazotized m-diamino-benzene adsorbed on a surface of the solid and chemically linked to the protein molecules. This invention also provides methods for reactivating inactivated biologically active material characterized by a water-insoluble solid with a surface to which has been adsorbed molecules of a diazotized aromatic amine chemically bonded to biologically active protein molecules. One method comprises a) adsorbing additional molecules of a diazotized aromatic diamine on said surface, and b) attaching fresh biologically active protein molecules to said additional molecules of diazotized aromatic diamines. Another method comprises a) treating said material with sodium dithionite to regenerate amine groups, and b) diazotizing said amine groups, and c) attaching thereto biologically active protein molecules.

36 Claims, No Drawings

WATER INSOLUBLE BIOLOGICALLY ACTIVE MATERIAL

The application is a continuation of the copending application, Ser. No. 379,403, filed July 13, 1973, now abandoned.

This invention relates to the bonding of biologically active molecules, such as enzymes, and enzyme derivatives to materials to render the molecules insoluble. More particularly the invention relates to materials to which biologically active molecules have been bonded.

BACKGROUND TO THE INVENTION

Enzymes are normally soluble in water and when they are used to catalyse reactions occurring in aqueous solutions, their recovery is often difficult and expensive. In some cases it may be necessary to remove the enzyme from the product and even its destruction may be a tedious procedure.

This is particularly important in the biochemical field where the recovery of metabolic intermediates, the protein enzymes that catalyse their conversion; and the hormones which often control a sequence of reactions is of major importance. There is also an increasing usage of protein antibodies in an insolubilized form in radioimmunassays for clinical diagnosis. When insolubilising biologically active molecules care must be taken to ensure that the bonding of the molecules to an insoluble carrier does not destroy or deleteriously modify the activity of the molecules.

The invention has been made with all the above points in mind.

BRIEF DESCRIPTION OF THE INVENTION

According to the invention there is provided a biologically active material which comprises a water-insoluble solid onto at least part of whose surface has been adsorbed a diazotized aromatic diamine, biologically active molecules having been chemically bonded to the diazotized aromatic diamine.

According to another aspect of the invention there is provided a method for preparing a biologically active material comprising adsorbing a diazotized aromatic diamine on at least part of the surface of a water-insoluble solid substrate, and bonding biologically active molecules to the diazotized aromatic diamine.

When the water-insolubilised biologically active molecules are proteins such as enzymes they make excellent catalysts and are particularly useful for catalysing reactions effected in aqueous solutions since the insoluble materials can be easly separated from the product and reused.

The biologically active molecules are capable of being chemically attached to the diazotized aromatic diamines without destroying the biologically-active sites of the molecules.

The attachment of the biologically active molecules to the carrier comprising the solid support and adsorbed diazotized diamines, is almost quantitative and unusually efficient. Thus a solution containing a high concentration of biologically active molecules can be used to provide a high concentration of active molecules on the carrier. Consequently the activity of the water-insoluble biologically active material can be high and the active materials can work very efficiently, efficiency being here calculated as a percentage of the activity which that amount of enzyme bound to the substrate would display in its original soluble form.

A large number of the biologically active molecules can be attached to the diazo groups of the diazotised aromatic diamine molecules without any activation immediately prior to bonding and the resulting chemical links hold the biologically active molecules to the carrier.

The invention is particularly surprising in view of the fact that soluble diazo groups are normally unstable, and yet the insolubilized diazo groups present in the biologically active material of the invention are relatively stable.

DESCRIPTION OF THE PREFERRED EMBODIMENT

The solid substrate can be, for example, in bead form. It can also be a pre-fabricated member such as a porous molecular sieve, tube, sheet, filter or membrane.

The biologically active material of the invention can naturally be mixed with substances having no biological activity or with material of the invention containing different active molecules.

One way of preparing the carrier, comprising solid substrate and adsorbed diazotized aromatic diamine, is to diazotise an aromatic diamine in the presence of the solid substrate. The diazotised aromatic diamine is strongly adsorbed on the surface of the substrate and can be freed from excess reactants by washing. This is the preferred process.

A second way of making the carrier of the invention is to diazotize an aromatic diamine before adsorbing the diazotised aromatic diamine on the surface of the solid substrate.

A third way is to absorb the aromatic diamine on the surface of the solid substrate, and remove any excess diamine by washing, and then diazotize the aromatic diamine. The biologicaly active molecules can then be attached to the carrier.

When the biologically active material of the invention has become inactive it can be reactivated by adsorbing additional diazotised aromatic diamine on the surface of the water-insoluble solid substrate, and then chemically attaching fresh biologically active molecules.

An alternative method of reactivating the biologically active material is to remove the inactivated biologically active molecules from the solid substrate by treatment with sodium dithionite, which regenerates amine groups on the solid substrate. The amine groups supplemented if required by absorbing additional aromatic diamine molecules, can then be diazotised and fresh biologically active molecules chemically attached.

The invention is particularly useful in the field of reactor separators where products of a reaction are separated as they are formed. A membrane such as a reverse osmosis membrane or a dialysis membrane may act as the solid support on the surface of which are adsorbed diazotised aromatic diamine molecules, biologically active molecules, such as enzymes, being chemically attached to the adsorbed diazotized molecules. The same enzymes can be attached to one or both faces of the membrane. Alternatively different enzymes can be attached to one face or to opposite faces of the membrane, so that as the products of an enzyme reaction occurring on one face of the membrane are formed they pass through the membrane and are catalysed by the enzymes attached to the opposite face.

The invention has the particular advantage when applied to membranes that the physical properties of the membranes are largely retained after adsorption of the diazotised aromatic diamines on their surfaces and attachment of the biologically active molecules. Furthermore, when the attached enzymes become inactivated the biologically-active membranes can be reactivated by the sodium dithionite treatment described above without substantially increasing the thickness of the membrane or otherwise altering its physical properties.

Particularly suitable membranes for forming the water-insoluble solid substrate of the biologically active material of the invention are, for example, cellulose dialysis membranes, and these can be mounted in apparatus for continuous dialysis. After adsorbing diazotised aromatic diamines on the membrane, enzymes can be attached to one or both sides of the membrane. Such biologically active membranes have a wide variety of uses in the biochemical field, such as, for example, in the hydrolysis of various dextrans. Reverse osmosis membranes made of cellulose acetate are also suitable, and it has been found, for example, that isoamylase can be attached to a cellulose (uprophan C) membrane; pullulanase on a cellulose acetate membrane; dextranase on an anionic polyelectrolyte membrane (Amicon UN2); dextranase on a polycarbonate film (types KG & G) and dextranase on a cellulose acetate membrane (Nillipore Pellicon).

The material which can be used as the water insoluble solid substrate is generally any material which can be dyed or redyed with diazotized aromatic diamines, such as solids containing free hydroxyl or polyamide groups. Particular examples include silica, i.e., sand, polysaccharide, cross-linked dextran, polyacrylamides, polyamides, polycarbonates, polyesters, glass (particularly porous glass), nylon, diatomaceous earth, natural or regenerated cellulose such as paper, Viscose Rayon, Sigmacell 38, Whatman CC31, Whatman CF11, Celite, Neosyl, Carboxymethyl cellulose, diethylaminoethyl cellulose, Bioglas-1000, Biogel P-6, Enzacryl gel $K_2$, cellulose acetate polyurethane, Sephades G-200, as well as inorganic hydrous oxides such as titanium oxide, zirconium oxide, aluminium oxide, and iron oxide. Generally all polar surfaces are dyeable as are the surfaces of natural products such as the cells of wood, e.g. balsa wood.

The preferred aromatic diamine for use in the invention is diamino-benzene, and the preferred isomer is meta-diamino benzene.

The biologically active molecules which can be used in the invention include proteins such as enzymes, coenzymes, lectins, and antibodies. Examples include, B-glucosidase, dextranase, amylase, glucamylase, catalase, glucose oxidase, thermolysin, N-acetyl amino acid amidohydrolase, peroxidase, chymotrypsin, uricase, pepsin, urease pronase, lactate dehydrogenase, cholinesterase, glucose isomerase, isoamylase and pullulanase, which may be used alone or in any combination.

After the preparation of the biologically active material of the invention any unreacted diazo groups on the Carrier should be made chemically inert, i.e. "annealed". This can be effected by treating the material with a phenol such as $\beta$-naphthol.

Diazotizaton of aromatic diamines is a well known process and can be carried out in the usual manner by treating the aromatic diamine with an inorganic acid and sodium nitrite at a low temperature.

With certain enzymes such as catalase and dextranase both the optimum pH for enzyme activity and the pH stability of the enzyme are modified considerably when the enzymes are insolubilised in the biologically active material. This effect is believed to be due to the residual amino groups of the diazotised aromatic diamine which have not been diazotized. This allows two enzymes in solution having different pH values to be used together since one enzyme can have its pH value reduced or increased to that of the other by bonding the enzyme to a diazotised aromatic diamine adsorbed on the water-insoluble solid.

The effectiveness of the biologically active material of the invention depends to a large extent upon its method of preparation. The absolute and relative amounts of aromatic diamine, sodium nitrite and hydrochloric acid, the area and type of water insoluble solid surface and the pH values employed are important and the optimum values of these can be found by experimentation for each water-insoluble solid, which is well within the capabilities of persons skilled in the art.

In order to achieve maximum enzyme insolubilization and efficiency, each carrier should be "optimised"; in other words the best reaction conditions and concentrations of reactants for preparing the carrier and adsorbed diazotised aromatic diamine should be found.

The attachment of the biologically active molecules to the diazotized aromatic diamine molecules depends upon the concentration and pH value of the solution containing the biologically active molecules to be attached to the diazotized aromatic diamine molecules and thus the optimum concentration of active molecules and pH should also be found for each enzyme.

It is believed, that the diazotised aromatic diamine molecules when adsorbed on the surface of the carrier exist as oligomers or high molecular weight species and that these molecules attach themselves to, and possibly surround, the carrier surface.

The higher the concentration of biologically active molecules in the solution offered to the diazotised aromatic diamine adsorbed on the surface of the carrier, the higher is the resulting concentration of attached biologically active molecules. A high concentration of biologically active molecules on the surface of the carrier tends to increase the adhesion of the molecules to the surface, provided a critical amount of sodium nitrite is employed, and thus reduces or prevents bleeding of the biologically actice molecules from the surface in the physiological range of pH. It furthermore reduces the degree of washing required before using the insolubilised enzyme and the need with certain enzymes to make free diazo groups chemically inert.

The ability of the insolubilised enzyme to catalyse reactions depends to a large extent upon the microenvironment of the enzyme on the carrier surface especially when the pH is varying. By the term "microenvironment" we mean the surrounding of the bound enzyme at a molecular level. The microenvironment can be varied in a number of ways. One way is to vary the nature of the aromatic diamine by, for example, by introducing cationic or anionic groups. A second way is to diazotise a mixture of the aromatic diamine and another functionalised aromatic derivative; and a third way is to use, instead of, $\beta$-naphthol in the annealing process, another functionalised aromatic derivative. The functionalised aromatic compound may be a nuclear substituted hydroxyl or amino aromatic compound containing cationic or anionic groups and substituted elsewhere in the molecule so that the compound is capable of reacting with a diazonium group.

The invention will now be illustrated with reference to the following Examples.

EXAMPLE 1 a. Adsorption of Diaminobenzene on Cellulose m-Diaminobenzene (10 g) was dissolved in dimethyl formamide (100 cm$^3$), and water (100 cm$^3$) and triethylamine (2.5 cm$^3$) were added. Cellulose (0.5 g) was slowly added to the stirred solution. After being stirred at room temperature overnight, the suspenson was filtered and the solid washed with dimethyl formamide until neutral, and then with water (200 cm$^3$). The solid was dried in vacuo over phosphorus pentoxide.

b. Coupling of β-Glucosidase to Cellulose/Diaminobenzene

Hydrochloric acid (1.0N, 2.0cm$^3$) was added to cellulose diaminobenzene (100 mg) and the suspension stirred at 0° C. Aqueous sodium nitrite (2% w/v, 2.0cm$^3$) precooled to 0° C, was slowly added and the suspension stirred for 15 minutes. The diazotised polymer was centrifuged down, the supernatant discarded, and ice-cold acetate buffer (0.2M, pH5.0, 5.0cm$^3$) added. After being stirred for a short while, the solid was centrifuged down and the washings discarded. This washing procedure was repeated twice.

β-Glucosidase (0.1mg/cm$^3$ in acetate buffer 0.2M, pH5.0, 5.0cm$^3$) was added to the washed polymer and the suspension stirred at 4° overnight. An aliquot (2.0cm$^3$) of a saturated solution of 2-naphthol in saturated sodium acetate solution was added and the mixture stirred for 15 minutes. The solid was washed with, and finally suspended, in acetate buffer (0.2M, pH5.0, 5.0cm$^3$).

The above procedure was repeated at five other pH values, the buffers used being phosphate pH 6.0, 7.0 and 8.0 and borate pH 9.0 and 10.0. The enzyme activity of each product is given in Table 1.

Table 1

| pH of coupling | 5.0 | 6.0 | 7.0 | 8.0 | 9.0 | 10.0 |
|---|---|---|---|---|---|---|
| Enzyme activity (moles of o-nitrophenol liberated in one hour by 20 mg product) | 8.4 | 9.7 | 8.6 | 7.7 | 5.5 | 4.5 | c. Stability of the Immobilized Enzyme at 37° C

Aliquots (0.50 cm$^3$) of a preparation coupled at pH 7.8 and a solution of free βglucosidase (20 mg/cm$^3$ in acetate buffer 0.2M, pH5.0), each containing one drop of toluene, were incubated at 37° C. At suitable intervals, O-nitrophenyl-β-D-glucopyranoside solution (2.0mg/cm$^3$ in acetate buffer 0.2M, pH5.0, 0.50cm$^3$) was added to an aliquot of each preparation for assay of enzyme activity by the normal method. The resultant enzyme activities are given in Table 2.

Table 2

| Days of incubation at 37° C | 0 | 1 | 2 | 3 |
|---|---|---|---|---|
| Enzyme activity of insolubilised preparation (as % of original) | 100 | 86 | 82 | 77 |
| Enzyme activity of soluble preparation (as % of original) | 100 | 40 | 12 | 2 | d. Reuse of the Water-Insoluble Enzyme Derivative

Aliquots (0.50 cm$^3$) of a preparation coupled at pH 7.8 were centrifuged and the supernatants discarded. O-Nitrophenyl-β-D-glucopyranoside solution (1.0 mg/cm$^3$ in acetate buffer 0.2M, pH5.0, 1.0cm$^3$) was added and the suspension stirred at 37° C. Aliquots (0.10 cm$^3$) of the supernatant were removed at zero time and after 15 minutes after centrifugation and added to sodium carbonate solution (0.2M, 0.50cm$^3$). The supernatant was then discarded and the above procedure repeated. This cycle was performed eight times. The optical density change at 420nm produced in 15 minutes incubation is expressed as a percentage of that of the first. The results are given in Table 3.

Table 3

| Times of reuse | 1 | 2 | 3 | 4 | 5 | 6 | 7 | 8 |
|---|---|---|---|---|---|---|---|---|
| Enzyme activity (as % of original) | 100 | 96 | 94 | 90 | 86 | 84 | 79 | 72 | e. Assessment for Leakage of Enzyme from Solid-phase into Solution

A preparation coupled at pH 7.8 (0.50 cm$^3$) was incubated at 37° C with o-nitrophenyl-β-D-glucopyranoside (2.0 mg/cm$^3$ in acetate buffer 0.2M, pH5.0, 0.50cm$^3$). After 60 minutes, the suspension was centrifuged and the supernatant dialysed at 4° in Visking Dialysis Tubing against five changes of acetate buffer (0.2M, pH5.0, 20cm$^3$). This procedure was repeated using acetate buffer (0.2M, pH5.0) instead of the substrate solution.

After dialysis, an aliquot (0.50 cm$^3$) was mixed with O-nitrophenyl-β-D-glucopyranoside (2.0 mg/cm$^3$ in acetate buffer 0.2M, pH5.0, 0.50cm$^3$) and incubated at 37° for 60 minutes. The amount of O-nitrophenol liberated was determined by removing an aliquot (0.50 cm$^3$), adding it to an equal volume of sodium carbonate solution (0.2M) and determining the optical density at 420 nm. The amount of O-nitrophenol obtained was so small as to be barely detectable.

f. Freeze-Drying of Water-Insoluble Enzymes

A preparation coupled at pH 7.8 (1.0cm$^3$) was centrifuged and the supernatant discarded. A solution of sorbitol (0.10 g/cm$^3$ in acetate buffer, 0.2M, pH5.0; 1.0cm$^3$) was added and the suspension freeze-dried. The product was washed three times with acetate buffer (0.2M, pH5.0; 1.0cm$^3$), suspended in the same buffer (1.0cm$^3$), and assayed for β-glucosidase activity in the normal manner. A sample (1.0cm$^3$) of the preparation which had not been freeze-dried was also assayed. The preparation retained 95% of its original activity.

EXAMPLE 2 a. Coupling of β-Glucosidase to Cellulose via Diazotized Diaminobenzene in the Presence of Triethylamine m-Diaminobenzene (100 mg) was dissolved in dimethylformamide (1.0 cm$^3$) in a stoppered test tube. Aqueous triethylamine (2.5% v/v; 1.0 cm$^3$) and cellulose ("Sigmacell" Microcrystalline Cellulose, Type 38; 100 mg) were then added. After washing down the sides of the tube with water (0.5 cm$^3$) the suspensions were allowed to stand at room temperature (22° ) overnight while being stirred magnetically. A control sample, prepared in exactly the same manner but with the omission of the m-diaminobenzene, was similarly treated.

After 16 hours the suspensions were centrifuged, the supernatants removed, and an extensive series of washings begun. Equal volumes of wash liquid were added to each tube, the tubes vigorously agitated on a vortex stirrer for one minute, and the suspensions then centrifuged. After removing and discarding the supernatants the procedure was repeated with fresh wash liquid. A cycle of ten washings was employed, the solids being subjected to alternate washing with dimethylformamide and water.

After removal of the final water-wash, hydrochloric acid (1.0 N; 2.0 cm³) was added to each tube and the suspensions stirred at 0° in an ice-bath. Precooled (0°) aqueous sodium nitrite (2% w/v; 2.0 cm³) was slowly added to each tube and the suspensions allowed to stir for thirty minutes. The diazotized material was then centrifuged down, the supernatant discarded, and ice-cold phosphate buffer (0.2 M, pH 6.0; 5.0 cm³) added. After stirring the suspension vigorously the solid was again centrifuged down and the washings discarded: this procedure was repeated twice. β-Glucosidase (0.2 mg/cm³ in phosphate buffer, 0.2M, pH 6.0; 5.0 cm³) was then added to each solid and the suspensions magnetically stirred at 4° for 16 hours.

β-Naphthol (saturated, in saturated sodium acetate; 2.0 cm³) was added to each solid and the suspensions allowed to stir for a further half-hour. The suspensions were then centrifuged, the supernatants discarded and the solids subjected to an exhaustive washing procedure. A cycle of ten washings was again employed, the wash liquids now being acetate buffer (0.2 M, pH 5.0; 5.0 cm³) and sucrose-salt in acetate buffer (0.2 M, pH 5.0, 1 M in sucrose and 1 M in sodium chloride; 5.0 cm³). Three further washes with acetate buffer were carried out, and the solids were then suspended in acetate buffer (0.2 M, pH 5.0; 5.0 cm³) prior to storage at 4°.

The enzymic activities of the solids were determined by assaying aliquots of the suspensions with O-nitrophenyl-β-D-glucopyranoside. Results are given in Table 5.

b. Coupling of β-Glucosidase to Cellulose via Diazotized Diaminobenzene Omitting the Intermediate Dimethylformamide/Water Washing Cycle m-Diaminobenzene (50 mg) was dissolved in hydrochloric acid (1.0 N; 2.0 cm³) and cooled to 0°. Precooled aqueous sodium nitrite (2% w/v; 2.0 cm³) was slowly added and the solution stirred for half an hour at 0°. β-Glucosidase (0.2 mg/cm³ in phosphate buffer, 0.2 M; pH 6.0; 5.0 cm³) was then added, followed by addition of cellulose (100 mg). The suspension was then stirred for sixteen hours at 4°.

A cellulose control was also prepared, following exactly the same procedure, but omitting the diaminobenzene.

β-Naphthol (saturated, in saturated sodium acetate; 2.0 cm³) was then added to each stirring suspension, and the suspensions allowed to stir for a further half-hour at 4°.

The exhaustive sucrose-salt/buffer washing procedure described in part (a) was then commenced.

On completion of the washing cycle the supernatant remained strongly red in colour: a further 29 washes with acetate buffer (0.2 M, pH 5.0) were therefore carried out. Even this extensive washing failed to remove all the colour from the supernatant. The method was therefore abandoned. No assay of any enzymic activity present on the solid was attempted.

c. Coupling of β-Glucosidase to Cellulose via Diazotized Diaminobenzene Using an Abbreviated Intermediate Washing Procedure m-Diaminobenzene (50 mg) was dissolved in hydrochloric acid (1.0. N; 2.0 cm³) and cooled to 0°. Precooled aqueous sodium nitrite (2% w/v; 2.0 cm³) was added and the solution stirred at 0° for half an hour. Cellulose (100 mg) was then added and the suspension stirred for a further fifteen minutes. The solid was then washed three times with ice-cold acetate buffer (0.2 M, pH 5.0: 3 × 5.0 cm³). After removing the final acetate wash β-glucosidase (0.2 mg/cm³) in phosphate buffer, 0.2 M, pH 6.0; 5.0 cm³) was added and the suspension stirred at 4° overnight.

A cellulose control was prepared following exactly the same procedure but omitting the diaminobenzene.

β-Naphthol was then added to each suspension as described in (a) and the exhaustive washing procedure was then commenced. After completion of the sucrose-salt/buffer washing cycle, an additional fifteen acetate buffer washes were required before the supernatants were sufficiently clear to permit assaying to be carried out.

The solids were finally suspended in acetate buffer (0.2 M, pH 5.0; 5.0 cm³). Assay of the β-glucosidase activity of the solids was carried out in the usual manner.

Results are given in Table 4.

Table 4.

Enzymic Activities Detected on Samples of Insolubilized β-Glucosidase.

| Example | Sample | Volume Assayed (cm³) | Change in Optical Density per Minute | % Enzymic Activity Detected |
|---|---|---|---|---|
| (a)(2) | "Test" (0.2 mg/cm³) | 1.0 | 0.00615 | 1.81 |
|  | "Control" (0.2 mg/cm³) | 1.0 | 0.00323 | 0.95 |
|  | "Soluble" (0.2 mg/cm³) | 1.0 | 0.00340 | 100. |
| (c) | "Test" (0.2 mg/cm³) | 1.0 | 0.0710 | 20.9 |
|  | "Control" (0.1 mg/cm³) | 1.0 | 0.0035 | 1.0 |
|  | "Soluble" (0.002 mg/cm³) | 1.0 | 0.0034 | 100. |

EXAMPLE 3 a. Coupling of β-Glucosidase to Cellulose via Diazotized Diaminobenzene by the Standard Procedure m-Diaminobenzene (50 mg), cellulose (100 mg) and hydrochloric acid (1.0 N; 2.0 cm³) were combined in a stoppered test tube equipped with a magnetic stirrer, and cooled to 0°. Pre-cooled (0°) aqueous sodium nitrite (2% w/v; 2.0 cm³) was then added and the suspension stirred at 0° for half an hour. The solid was then washed three times with ice-cold acetate buffer (0.2M, pH 5.0; 3×5.0 cm³) and β-glucosidase (0.2 mg/cm³; 5.0 cm³) added as in example 2/C. The suspension was allowed to stir for sixteen hours at 4° prior to addition of β-naphthol in the usual manner.

A cellulose control was prepared following the same procedure but omitting the diaminobenzene.

Washing with sucrose-salt and acetate buffer was carried out as described in Example 2(b). The number of washes required was the same. The solids were suspended in acetate buffer (0.2 M, pH 5.0; 5.0 cm³). Assay of enzymic activity on the solids was performed in the usual manner. Results are given in Table 5.

a. Coupling of β-Glucosidase to Cellulose by the Standard Method Using a More Concentrated Solution of Enzyme The procedure previously described was followed. β-Glucosidase (10 mg/cm³ in acetate buffer, 0.2 M, pH 5.0; 0.5 cm³) was added to the diazotized diaminobenzene/cellulose preparation. Use of more concentrated enzyme solution was found to facilitate washing: the cycle of sucrose-Salt/buffer washes described in Example 2D was found to be sufficient to remove all visible colour from the supernatants.

Enzymic activities on the diaminobenzene preparation and on a control solid (prepared without the addition of diaminobenzene) were determined in the usual manner. Results are given in Table 5.

| Example | Sample | Volume Assayed (cm³) | Change in Optical Density per minute | %enzymic activity detected |
|---|---|---|---|---|
| (a) | Test (0.2 mg/cm) | 1.0 | 0.070 | 20.6 |
| | "Control" (0.2 mg/cm³) | 1.0 | 0.003 | 0.9 |
| | "Soluble" (0.002 mg/cm³) | 1.0 | 0.0034 | 100. |
| (a) | "Test" (1.0 mg/cm³) | 0.35 | 0.296 | 24.2 |
| | "Control" (1.0 mg/cm³) | 0.35 | 0.008 | 0.6 |
| | "Soluble" (1.0 mg/cm³) | 0.35 | 1.224 | 100. | b. Determination of the Optimum Coupling Time for the Preparation of Water-Insoluble β-Glucosidase The standard method of diazotization was followed, six samples of solid (100 mg cellulose) being prepared. After washing the diazotized cellulose/diaminobenzene preparations three times with buffer, β-glucosidase (10 mg/cm³ in acetate buffer, 0.2 M, pH 5.0; 0.5 cm³) was added. The length of time the enzyme was left in contact with the solid was varied: coupling times of 0.5, 1.0, 2.0, 4.0, 5.5 and 22.0 hours were employed. Coupling was said to have been "completed" on addition to each tube of an aliquot (2.0 cm³) of a saturated solution of β-naphthol in saturated sodium acetate. Annealing was allowed to proceed for 24 hours in all cases. On completion of the annealing process the solids were washed and assayed in the usual manner. Results are given in Table 6.

TABLE 6

Enzymic Activities Detected on Samples of Insolubilized β-Glucosidase Prepared Using Different Coupling Times

| Coupling Time (hours) | Volume Assayed (cm³) | Change in Optical Density per Minute | Total Units of Activity Detected | % Enzymic Activity Detected |
|---|---|---|---|---|
| 0.5 | 0.10 | 0.290 | 56.5 | 37.6 |
| 1.0 | 0.10 | 0.333 | 63.6 | 42.4 |
| 2.0 | 0.10 | 0.380 | 73.1 | 48.7 |
| 4.0 | 0.10 | 0.319 | 61.4 | 40.8 |
| 6.0 | 0.10 | 0.274 | 54.2 | 36.1 |
| 22.0 | 0.10 | 0.242 | 47.2 | 31.4 |
| Soluble enzyme (1.0 mg/cm³) | 0.05 | 0.744 | 150.0 | 100.0 | c. Determination of the Optimum Annealing Time for the Preparation of Water-Insoluble β-Glucosidase The standard method of diazotization and coupling was followed, a coupling time of two hours being allowed. The length of time the solids were left to anneal with β-naphthol at 4° was varied: annealing times of 1.0, 2.0, 3.0, 4.5 and 23.0 hours were employed. The solids were then washed and assayed in the usual manner. Results are given in Table 7.

TABLE 7

Enzymic Activities Detected on Samples of Insolubilized β-Glucosidase Prepared Using Different Annealing Times (with β-Naphthol)

| Annealing Time (hours) | Volume Assayed (cm³) | Change in Optical Density per Minute | Total Units of activity Detected | % Enzymic Activity Detected |
|---|---|---|---|---|
| 1.0 | 0.05 | 0.156 | 61.4 | 40.8 |
| 2.0 | 0.05 | 0.120 | 47.2 | 31.5 |
| 3.0 | 0.05 | 0.168 | 71.0 | 47.3 |
| 4.5 | 0.05 | 0.178 | 70.8 | 47.1 |
| 23.0 | 0.05 | 0.166 | 70.6 | 47.0 |
| Soluble enzyme (1.0 mg/cm³) | 0.025 | 0.372 | 150.0 | 100. | d. Investigation of the Effect on the Activities of Solid-Phase β-Glucosidase of "Self-Annealing" at Room Temperature The standard method of diazotization and coupling was followed as for Example 3(c). β-Naphthol was not added to the solids on completion of coupling: the solids were instead allowed to warm to just above room temperature (approximately 28°) and were then left to stir for variable periods (1.0, 2.0, 4.5 and 23.0 hours) before normal washing and assaying procedures were begun. Results are given in Table 8.

Table 8

Enzymic Activities Detected on Samples of Insolubilized β-Glucosidase Prepared Using Different Annealing Times (Without β-Naphthol).

| Annealing Time (hours) | Volume Assayed (cm³) | Change in Optical Density per minute | Total Units of Activity Detected | % Enzymic Activity Detected |
|---|---|---|---|---|
| 1.0 | 0.05 | 0.126 | 52.0 | 34.7 |
| 2.0 | 0.05 | 0.084 | 37.8 | 25.2 |
| 4.5 | 0.05 | 0.116 | 47.2 | 31.4 |
| 23.0 | 0.05 | 0.135 | 56.6 | 37.8 |
| Soluble enzyme (1.0 mg/cm³) | 0.025 | 0.372 | 150.0 | 100.0 | e. Determination of the Optimum Amount of Hydro-chloric Acid Required for Successful Diazotization Prior to Coupling with β-Glucosidase The usual method of diazotization and coupling was followed but the concentration of the solution of hydrochloric acid employed in the initial diazotization step was varied. The amounts of acid added (in 2.0 cm³ of water) to the cellulose (100 mg) and diaminobenzene (50 mg) were 0.002 moles (normal amount), 0.0025 moles, 0.004 moles and 0.005 moles. The usual coupling (2 hours), annealing (4.5 hours), washing and assaying procedures were followed. Results are given in Table 9.

Table 9

Enzymic Activities Detected on Samples of Insolubilized β-Glucosidase Prepared Using Different Amounts of Hydrochloric Acid in the Diazotization Step.

| Moles of Hydrochloric Acid | Volume Assayed (cm³) | Change in Optical Density per Minute | Total Units of Activity Detected | % Enzymic Activity Detected |
|---|---|---|---|---|
| 0.0020 | 0.05 | 0.144 | 56.6 | 37.8 |
| 0.0025 | 0.05 | 0.156 | 61.4 | 40.9 |
| 0.0040 | 0.05 | 0.134 | 56.4 | 37.5 |
| 0.0050 | 0.05 | 0.103 | 42.4 | 28.3 |
| SOluble enzyme (1.0 mg/cm³) | 0.025 | 0.372 | 150.0 | 100.0 | f. Determination of the Optimum Amount of Sodium Nitrite Required for Successful Diazotization Prior to Coupling with β-Glucosidase The usual method of diazotization and coupling was followed, but the amounts of sodium nitrite added to each of five tubes were varied. Cellulose/diaminobenzene was treated with 0.00156 moles, 0.00130 moles, 0.00104 moles, 0.00087 moles and 0.00058 moles (usual amount) of sodium nitrite dissolved in water (2.0 cm³). Two-hour long coupling was allowed and the solids were annealed for 18 hours. Washing and assaying were carried out as usual. Results are given in Table 10.

Table 10

Enzymic Activities Detected on Samples of Insolubilized β-Glucosidase Prepared Using Different Amounts of Sodium Nitrite.

| Moles of Sodium Nitrate | Volume Assayed (cm³) | Change in Optical Density per Minute | Total Units of Activity Detected | % Enzymic Activity Detected |
|---|---|---|---|---|
| 0.00058 | 0.05 | 0.181 | 75.6 | 50.5 |
| 0.00087 | 0.05 | 0.156 | 61.4 | 40.9 |
| 0.00104 | 0.05 | 0.169 | 70.8 | 47.2 |
| 0.00130 | 0.05 | 0.201 | 80.4 | 53.5 |
| Soluble enzyme (1.0 mg/cm³) | 0.025 | 0.372 | 150.0 | 100. | g. Determination of the Optimum Amount of Diaminobenzene Required for Successful Coupling of β-Glucosidase to Cellulose The usual method of diazotization and coupling was employed, but the amount of diaminobenzene offered to the solid was varied. Two sets of experiments were carried out: three samples of cellulose (100 mg in each case), combined with m-diaminobenzene (10.0 mgs, 25.0 mgs, 50.0 mgs) in hydrochloric acid (1.0 N; 2.0 cm³ in each case), were treated with sodium nitrite (6% w/v in water; 0.40 cm³, 1.0 cm³, 2.0 cm³). In the second experiment the same quantities of solids were used and the same conditions applied, but the strength of the solution of sodium nitrite was reduced by three times (i.e. 2% w/v sodium nitrite in water was used). The amount of hydrochloric acid was kept constant in all cases.

Diazotization, coupling, annealing and washing were carried out in the usual manner. The enzymic activities of the solids were determined immediately after washing and again exactly one week later. The results are given in Table 11.

Table 11

Enzymic Activities Detected on Samples of Insolubilized β-Glucosidase Prepared Using Different Amounts of Diaminobenzene.

| Amount of Diaminobenzene (mg) Offered to 100 mg of Cellulose | Molar Ratio of Sodium Nitrate to Diaminobenzene | % Enzymic Activity Detected Initially | % Enzymic Activity Detected After One week |
|---|---|---|---|
| 10.0 | 3.77 | 8.8 | 7.2 |
| 10.0 | 1.29 | 15.6 | 15.1 |
| 25.0 | 3.77 | 27.5 | 24.0 |
| 25.0 | 1.29 | 28.2 | 23.3 |
| 50.0 | 3.77 | 56.2 | 49.0 |
| 50.0 | 1.29 | 56.2 | 45.9 |

*The insolublized enzyme preparations were stored in suspension in acetate buffer (0.2m, pH 5.0) at 4° for one week.

h. Determination of the Optimum Amount of β-Glucosidase Required for the Successful Coupling of the Enzyme to Cellulose The usual method of diazotization and coupling was employed, using a two-hour long coupling period. The amounts of enzyme offered to each of the six samples of cellulose/diaminobenzene (100 mg cellulose) were varied: 1.0 mg. 3.0 mg, 4.0 mg, 5.0 mg, 8.0 mg and 10.0 mg quantities of enzyme, dissolved in acetate buffer (0.2 M, pH 5.0; 0.5 cm³) were added to the diazotized material. After annealing with β-naphthol for 4.5 hours the solids were washed in the usual manner and the enzymic activities of each preparation were determined. Results are given in Table 12.

Table 12.

Enzymic Activities Detected on Samples of Insolubilized β-Glucosidase Prepared by Offering Different Amounts of Enzyme to Diazotized Diaminobenzene/Cellulose.

| Amount of Enzyme Offered | | Volume Assayed (cm³) | Change in Optical Density per Minute | Total Units of Activity Detected | % Enzymic Activity Detected |
|---|---|---|---|---|---|
| Units of Activity | Mgs | | | | |
| 30.0 | 1.0 | 0.02 | 0.0264 | 31.0 | 103 |
| 90.0 | 3.0 | 0.02 | 0.0559 | 66.5 | 74 |
| 120.0 | 4.0 | 0.02 | 0.0699 | 82.6 | 69 |
| 150.0 | 5.0 | 0.02 | 0.0705 | 84.0 | 56 |
| 240.0 | 8.0 | 0.02 | 0.0738 | 87.0 | 36 |
| 300.0 | 10.0 | 0.02 | 0.0639 | 73.7 | 25 |

EXAMPLE 4 m-Diaminobenzene (0.1gms) was reacted with "Sigmacell" microcrystalline cellulose (0.1gms) in the presence of dimethylformamide (1.0mls), triethylamine (0.025mls) and water (1.0mls). After having been stirred at room temperature overnight, the suspension was centrifuged, the supernatant removed and the solid washed thoroughly, first with dimethylformamide (six times) and then with water (six times). A control was also prepared in exactly the same way omitting the diaminobenzene.

Cellulose/diaminobenzone test and cellulose control were each diazotised: 2.0cm³ of 1.0N hydrochloric acid was added to each of the tubes and the suspensions stirred at 0° C. Precooled aqueous sodium nitrite (2% w/v; 2.0cm³) was then slowly added to each tube and the suspensions stirred for thirty minutes. Both were then centrifuged down and the supernatants discarded. Icecold buffer (0.2M, 5.0cm³, acetate buffer pH 5) was added and the suspensions vigorously stirred. After centrifuging and removing the supernatants this washing procedure was repeated twice. After removing the final wash, 5.0cm³ of a solution of enzyme (0.2mg/cm³ in 0.2M phosphate or acetate buffer) was then added to each tube and the suspensions stirred at 4° C overnight.

2.0cm³ of a saturated solution of β-naphthol in saturated sodium acetate solution was added to each tube and the suspensions stirred for half an hour. The solids were then washed thoroughly: five cycles of alternate washing with acetate buffer (0.2M, pH5.0; 5.0cm³) and a solution of M sodium chloride and M sucrose in acetate buffer (0.2M, pH5.0; 5.0cm³) were carried out. The solids were finally washed twice more with acetate buffer and then suspended in the acetate buffer (0.2M, pH5.0; 5.0cm³).

The substrate used was β-nitrophenyl-β-D-glucopyranoside (2.0mg/cm³). 1.0mls of each of the cellulose and cellulose/diaminobenzene suspensions were incubated with 1.0mls of substrate for periods of 30 and 45 minutes at 29° C. Three control assays were also carried out, two on tubes containing known amounts of enzyme in acetate buffer, pH 5.0, and one on a solution of buffer alone. At thirty minutes and forty-five minutes 500μl aliquots were taken from each tube and added to tubes containing 1.0mls of sodium carbonate (0.2M). The optical densities of the supernatants after centrifuging were determined at 420nm against a water blank. (Table 13).

Table 13

Optical densities of supernatants after incubation of β-glucosidase enzyme preparations with substrate at pH 5.0, followed by addition of $Na_2CO_3$.

| Tube | Optical Density at 30 minutes (420nm) | Optical Density at 45 minutes (420nm) |
| --- | --- | --- |
| Controls | | |
| 0.0002mg enzyme | 0.095 | 0.141 |
| 0.0001mg enzyme | 0.040 | 0.058 |
| acetate buffer | 0.005 | 0.000 |
| cellulose-enzyme | 0.058 | 0.079 |
| Test | | |
| cellulose-DAB-enzyme | 0.397 | 0.597 |

Activity is thus seen to be present on the cellulose/diaminobenzene/enzyme polymer.

EXAMPLE 5

Method (a):

0.05gms diaminobenzene was dissolved in hydrochloric acid (1.0N; 2.0cm³) in a stoppered test tube and cooled in ice to 0° C. Aqueous sodium nitrite (2% w/v; 2.0cm³) (previously cooled to 0° C) was added slowly with magnetic stirring and the solution stirred for half an hour at 0° C. β-Glucosidase (0.2mg/cm³ in phosphate buffer (0.2M, pH6.0) 5.0cm³) was then added followed by 0.1gms of "sigmacell" microcrystalline cellulose and the suspension stirred overnight at 4° C.

Method b 0.05 gms diaminobenzene was dissolved in hydrochloric acid (1.0N; 2.0cm³) in a stoppered test tube and cooled to 0° C with stirring. Precooled (0° C) aqueous sodium nitrite (2% w/v; 2.0cm³) was added and the suspension stirred at 0° C for half an hour. Cellulose (0.10gms) was then added and the suspension stirred for a further 15 minutes. The solid was then washed three times with icecold acetate buffer (0.2M, pH5.0; 3 × 5.0cm³). The suspensions were centrifuged and the supernatants discarded. Buffer was then added and the suspensions vigorously agitated for one minute on a "Vortex" stirrer. The suspension was again centrifuged and the wash liquor removed by pipette and discarded. After removing the final acetate wash β-glucosidase (0.2mg/cm³ in phosphate buffer (0.2M, pH6.0; 5.0cm³) was added and the suspension stirred at 4° C overnight.

Method c 0.05gms diaminobenzene, 0.10gms "Sigmacell" cellulose and hydrochloric acid (1.0N, 2.0cm³) were combined in a stoppered test tube. Precooled (0° C) aqueous sodium nitrite (2% w/v, 2.0cm³) was then added and the suspension stirred at 0° C for half an hour. The solid was then washed three times with icecold acetate buffer (0.2M, pH5.0, 3 × 5.0cm³), and β- glucosidase (0.2mg/cm³, 5.0cm³) added as for Method (b). The suspension was left to stir overnight at 4° C.

A control was also prepared for each method following exactly the same procedures described above but omitting the diaminobenzene. β-Naphthol (saturated, in saturated sodium acetate; 2.0cm³) was added to each tube the following morning. The suspensions were stirred for 30 minutes and the solids then subjected to the exhaustive washing procedure previously used, i.e., five cycles of alternate washing with acetate buffer (0.2M, pH5.0; 5.0cm³) and a solution of M sodium chloride and M sucrose in acetate buffer (0.2M, pH5.0, 5.0cm³) were carried out. The solids were washed twice more with acetate buffer and then suspended in 5.0cm³ of buffer. Thus far the wash procedure followed was identical to that used in Example 2. However, the supernatants of the three suspensions involving diaminobenzene, despite this extensive washing, still remained red (a) or yellow (b and c) in colour. It was decided to repeat the whole sucrose-salt/acetate washing cycle. This was done and the cycle followed by five acetate washes. The supernatant however, remained orange in colour. When it still was not colourless after an additional fourteen washes with acetate, Method (a) was abandoned and no assay of its enzymic activity attempted. Total numbers of washes to which each solid was subjected during the sucrose-salt/acetate wash cycles were as follows:

Method a: (abandoned "Control a" :13
Method b: "Control b" :13
Method of c: "Control c" :13

The solids (all dark red in colour) were finally suspended in acetate buffer (0.2M, pH5.0; 5.0cm³).

The enzymic activity present on a sample of each control polymer suspension a, b, c and on samples from methods b and c were then determined.

The substrate was used β-nitrophenyl-β-D-glucopyranoside (2.0mg/cm³ in acetate buffer, 0.2M, pH5.0). 1.0cm³ of each of the cellulose and cellulose/diaminobenzene suspensions were incubated with 1.0cm³ of substrate for periods of 30 and 45 minutes at 29° C. Three control assays were also carried out, two on tubes containing known amounts of enzyme in acetate buffer, pH5.0, and one on a solution of buffer alone. In addition 1.0cm³ of each of the Method b and Method c suspensions were incubated with 1.0cm³ acetate buffer (i.e., no substrate added) and their optical densities read: these controls permitted an estimation of the extent of residual colour remaining despite the wash procedure. At 30 minutes and 45 minutes 500/1 aliquots were taken from each tube and added to tubes containing 1.0cm³ of sodium carbonate (0.2M). The optical densities of the supernatants after centrifuging were determined at 420nm (Table 14).

Table 14.

Optical densities of supernatants after incubation of
φ-nitrophenyl-β-D-glucopyranoside with enzyme preparation followed
by addition of 0.5cm³ aliquets to sodium carbonate solution (incubation
at 29° C, pH5.0) (420nm, against a water blank).

| | Tube | Optical Density at thirty minutes (water blank) | Optical Density at 45 minutes (water blank) |
|---|---|---|---|
| Controls | 0.002mg/cm³ enzyme | 0.092 | 0.130 |
| | 0.001mg/cm³ enzyme | 0.051 | 0.072 |
| | acetate buffer | 0.007 | 0.006 |
| | cellulose enzyme (a) | 0.044 | 0.056 |
| | cellulose enzyme (b) | 0.106 | 0.121 |
| | cellulose enzyme (c) | 0.093 | 0.112 |
| Tests | cellulose-DAB-enzyme (b) | 2.15 | 2.30 |
| | cellulose-DAB-enzyme (b) | 2.13 | 2.30 |
| | cellulose-DAB-enzyme (c) | 2.09 | 2.27 |
| | cellulose-DAB-enzyme (c) | 2.30 | 2.30 |
| Controls without Substrade Addition | | | |
| | cellulose-DAB-enzyme (b) | 0.070 | 0.077 |
| | cellulose-DAB-enzyme (c) | 0.104 | 0.018 |

It is clear from these results that there is a considerable degree of enzymic activity present on the cellulose-diaminobenzene-enzyme polymer whether prepared by Method b or Method c.

The application of Method (c) to coupling β-glucosidase to "Sigmacell" cellulose was repeated and the enzymic activity of the preparation compared with that of controls.

Four tubes were prepared as follows:
I. 0.25cm³ "control" suspension, 0.75cm³ buffer
II. 0.25cm³ "test" suspension, 0.75cm³ buffer
III. 0.25cm³ soluble enzyme (0.25/cm³), 0.75cm³ buffer
IV. 1.00cm³ buffer To each tube at known time was added 3.0cm³ of substrate (2.0mg/cm³ o-nitrophenyl-β-D-glucopyranoside made up in acetate buffer, pH5.0). Aliquots of the suspensions were withdrawn at known times and transferred to tubes containing equal (0.5cm³) volumes of sodium carbonate (0.2M). The assay was carried out at 37° C. Optical densities were read at 420nm against a water blank (Table 15).

Table 15

Enzymic Activities on the Solid Phase β-Glucosidase/sigmacell
Preparations as Determined on Assaying with O-Nitrophenyl-β-D-Glucopyranoside.

| Sample | Enzymic Activity (Units*/mg protein) | %Activity** (relative to soluble enzyme) |
|---|---|---|
| Control: cellulose/enzyme | 0.21 | 1.1 |
| Test: cellulose/DAB/enzyme | 7.90 | 42.0 |
| Soluble enzyme | 19.30 | 100.0 |

(*Units - change in optical density reading per minute.)
(*Assuming that all the enzyme (5 mg) added to the diazotised cellulose DAB preparation coupled onto the solid successfully).

EXAMPLE 6

Duplicate samples of Sigmacell 38 (100mg), Whatman CC31 (100mg), and Whatman CF11 (100mg) were weighed into stoppered tubes to each of which were added m-diaminobenzene (50mg) and hydrochloric acid (N, 2ml). Further operations were carried out at 0°. Aqueous sodium nitrite (2% w/v, 2ml) was then added to one of the tubes containing Sigmacel 38, Whatman (C31, and Whatman CF11, the second tubes containing these celluloses being kept as a control. After stirring for 0.5 hours the solid in all six tubes was washed four times with ice-cold phosphate buffer (25mM, pH7.5, 15ml) containing EDTA (1CmM). After decanting the final washing aliquots, (0.2ml) of a solution of urease (20mg/ml) in the same phosphate buffer was added to each tube and the suspensions left to stir overnight at 0°-4°. Next day aliquots (10ml) of a saturated solution of β-naphthol in saturated sodium acetate was added and the stirring continues for 0.5 hours. The samples were then washed twelve times with phosphate buffer (25mM, pH7.5, 15ml) containing EDTA (5mM). Each washing was of 20 minutes duration and carried out with vigorous magnetic stirring. The samples were finally suspended in the same buffer (10ml).

Suspensions (1mg/ml) of the conjugates or controls to be assayed were prepared in phosphate buffer (25mM, pH7.5) containing EDTA (5mM). Aliquots (1.5ml) of these suspensions were pipetted into a stirred solution of urea (150mM. 27ml) in phosphate buffer (100mM, Ph7.5) containing EDTA (5mM). The digest was maintained at 30° and samples (1.5ml) were removed at times 0, 5, 10, 20 and 30 minutes, each being immediately centrifuged and part of the supernatant (1ml) diluted with distilled water (9ml) and Nesslers reagent (1ml). The colour yield (480nm) was related to ammonia concentration by means of a standard graph. Digests involving cellulose/diaminobenzene conjugates were also tested for urease activity re-solubilized on contact with the substrate by removing aliquots from the digests after 20 minutes, centrifuging to remove the conjugate, and incubating the supernatant for a further hour, after which the ammonia content was again assayed. Subsequently, the water-soluble urease remaining in the digests was recovered and resuspended in fresh buffered urea solutions. In this way the digestion and assay procedure was repeated twice. All results are presented in Table 16.

Table 16

| Grade of cellulose | Activity of conjugate enzyme units/ g conjugate | Protein bound mg/g conjugate | Activity of bound enzyme enzyme units/ mg bound protein | % activity retained on coupling |
|---|---|---|---|---|
| CC31 | 196.5[a] | 43.5 | 4.5 | 151 |
| Sigmacell | 216[b] | 50.2 | 4.3 | 145 |
| CP11 | 154[c] | 43.4 | 3.55 | 119 |

Activity of the native enzyme = 2.98mg NH₃/minute/mg enzyme. 1 unit of activity is the amount of enzyme that will produce 1mg of ammonia per minute in a 0.15M urea solution at 30°: pH7.5.
a 2nd use, 198, 3rd use, 196
b 2nd use, 156, 3rd use, 211
c 2nd use, 127, 3rd use, 123.

a. Whatman CC31/Diaminobenzene urease conjugate

This was prepared as detailed above except that the β-naphthol annealing procedure was omitted. A non-diazotised sontrol was included. Conjugate and control were assayed.

b. Whatman CC31/diaminobenzene/thermolvsin conjugate

This was prepared in similar manner to the urease conjugate in (a). However, twenty buffer washings of the thermolysin conjugate were necessary before colour was no longer apparent in the supernatant.

c. Whatman CC31/diaminobenzene/N-acetyl L-amino acid amidohydrolase conjugate The coupling and washing procedures were precisely those described for the urease conjugate in (a).

containing $CaCl_2$ (20mM). A check for supernatant activity was performed as described above.

Assay of cellulose CC31/diaminobenzene/N-acetyl L-amino acid amidohydroclase conjugate and control for acylase activity Suspensions (20mg/ml) of the conjugate and control were centrifuged down, the supernatants discarded, and each re-constituted with a solution (25mM, 5ml) of N-acetyl-L-methionine in phosphate buffer (50mM, pH7.0). The digests were stirred at 30° during which samples (0.2ml) were taken at 0, 5, 10, 20, and 30 minutes each sample being pipetted into pre-heated citrate buffer (0.2M, pH5.0, 1ml) which was maintained at 100° for 5 minutes. Later, the tubes were further diluted with $H_2O$ (0.8ml) followed by Moore and Stein ninhydrin reagent (1ml). The tubes were then heated for 20 minutes on a boiling water bath, cooled rapidly and read at 570nm. The L-methionine concentration in the digests was estimated by means of a standard graph. The conjugate was also tested for acylase activity re-solubilisation in contact with the substrate by removing a sample of the digest at 20 minutes centrifuging and further incubating the supernatant in the usual way.

The results of (a), (b) and (c) are given in the following Table 17.

Table 17

| Enzyme | Activity of native enzyme enzyme units/ mg enzyme | Activity of conjugate enzyme units/ mg enzyme | Protein bound mg/g conjugate | Activity of bound enzyme enzyme units/ mg bound protein | % activity retained on coupling |
|---|---|---|---|---|---|
| Urease | 2.93 | 71 | 36.6 | 1.94 | 65 |
| Thermolysin | 39.5 | 57.5 | 10.5 | 5.48 | 14 |
| Acylase | 0.47 | 2.5 | 36.2 | 0.069 | 15 |

(i) Urease
1 Unit of activity is the amount of enzyme that will produce 1mg of ammonia per minute in a 0.15H urea solution at 30°, pH7.5.
(ii) Thermolysis
1 Unit of activity is the amount of enzyme that will produce an extinction (280nm) change of 1.0 unit per minute in 1cm³ of 1% casein solution at 30°, pH7.25 after the digestion has been stopped with 1.5cm³ of aqueous 5% trichloroacetic acid 1cm cells are used to read the extinction.
(iii) Asylase
1 Unit of activity is the amount of enzyme that will produce 1mg of l-methionine per minute in a 25mM N-acetyl-L-methionine solution at 30°, pH7.0.

Assay of cellulose CC31/diaminobenzene/thermolysin conjugate and control for caseinolvtic activity Suspensions (1mg/ml) of the conjugate and control were prepared in Tris buffer (50mM, pH7.5) containing $CaCl_2$ (10mM). Aliquots (0.5ml) of the suspensions were pipetted into casein solution (1% w/v, 10ml) in Tris buffer (50mM, pH7.25) containing $CaCl_2$ (10ml). The digests were magnetically stirred at 30°. At times 0, 5, 10, 20, 30, and 40 minutes the digests were quickly centrifuged and a sample (1ml) of supernatant pipetted into TCA (5% w/v, 1.5ml). The centrifuges samples were later read at (280nm). Digests were tested for re-solubilised caseinolytic activity after 20 minutes by taking samples (1ml), centrifuging, incubating the supernatant for a further hour at 30°, and re-assaying with TCA. The results are presented in Table 8. Since considerable activity was resolubilised, the whole conjugate was subjected to a further 5 washings with casein solution (1% w/v, 15ml) in the above buffer. Subsequently, samples (1mg) of the conjugate were suspended in casein solution 1%, 5ml) in Tris buffer, Tris buffer alone (5ml), and a solution (2nM, 5ml) of a furacryloylglycylleucinamide in Tris buffer. After stirring for 20 minutes the mixtures were centrifuged and aliquots (4ml) of the various supernatants diluted with an equal volume of casein solution (2%) in Tris buffer

EXAMPLE 7 a. Linkage of Dextranase to Cellulose using concentrated enzyme solution

Diaminobenzene (0.05gms), "Sigmacell" cellulose (0.10gms) and hydrochloric acid (1.0M, 2.0cm³) were combined in a stoppered test tube. Pre-cooled (0° C) aqueous sodium nitrite (2% w/v, 2.0cm³) was added and the suspension stirred at 0° C for 30 minutes. The solid was then washed three times with acetate buffer (0.2M, pH5.0, 3 × 5.0cm³; pre-cooled to 0° C). Dextranase (10mg/cm³ in buffer, 0.5cm³) was added and the suspension left to stir at 4° C for 18 hours.

Two controls were simultaneously prepared. For both the same procedure as above was followed but for "Control A" the diaminobenzene was omitted and for "Control B" the enzyme was omitted and replaced by 0.5cm³ of buffer.

On addition of sodium nitrite both the "test" and "Control B" suspensions changes from white to wine-red in colour. "Control A" remained unchanged in colour.

The following morning β - naphthol (saturated in saturated sodium acetate; filtered through a No. 4 sinter, 2.0cm³) was added to each tube and the suspensions stirred for 30 minutes at room temperature. No colour changes were observed. The solids were then subjected to the usual washing procedure: five cycles of alternate washings with "neat" acetate buffer (0.2M, pH5.0) and a solution 1M in sodium chloride and 1M in sucrose in the same buffer, followed by five successive washes with "neat" acetate buffer. All wash solutions were ice-cold. Each "wash" involved addition of the wash solution to the solid, through mixing of the suspension on a vortex stirrer, and removal of the supernatant after centrifugation. For the "Test" and "Control B" suspensions the sucrose/sodium chloride/buffer wash supernatants were pink in colour, and those from the "neat" buffer washes colourless after the final washing. Washings from the "Control B" solid remained colourless throughout. When the washing cycle had been completed the solids were suspended in acetate buffer (0.2M, pH5.0; 5.0cm³) and the enzymic activity on each solid assayed.

b. Determination of dextranase activity

Dextranase activity was determined by measuring the initial rate of hydrolysis at 37° C of a solution of dextran (0.5%) in acetate buffer (0.2M, pH5.0). The rate of formation of reducing sugar was determined by assaying aliquots of the digests with dinitrosalicylate reagent (0.25gms 3, 5-dinitrosalicyclic acid, 50cm³ 2.0N NaOH, 75 gms sodium potassium tartrate, made up to a total volume of 250cm³ and then stored in the cold in a dark bottle).

Aliquots of each solid suspension (100mg/cm³ cellulose; 200µ.1) were incubated with substrate solution (2.5cm³) and stirred at 37° C. Samples of the stirred suspensions (500µ1) were taken at intervals of 0, 15 and 30 minutes and transferred to tubes containing 2.5cm³ of dinitrosalicylate (DNS) reagent. An aliquot of a standard dextranase solution (1mg/cm³,200µ1) and an aliquot of "neat" acetate buffer (200µ1) were treated simultaneously, to provide an assay standard and an assay blank respectively. When all samples had been taken the tubes were mixed thoroughly and then heated for 10 minutes on a boiling water bath. After cooling to room temperature, each tube containing solid was centrifuged, and the optical densities of the supernatants determined at 570nm using an S.P.500 spectrophotometer (Table 18).

Table 18

Enzymic Activities on the Solid Phase Dextranase/Sigmacell Preparations as Determined on Assaying with Dinitrosalicylate Reagent

| Sample | Enzymic Activity (Units*/mg** protein) | % Activity** (relative to soluble enzyme) |
|---|---|---|
| Control: cellulose/enzyme | 0.24 | 1.67 |
| Control: cellulose/DAB | 0.00 | 0.00 |
| Test: cellulose/DAB/enzyme | 2.32 | 16.03 |
| Soluble enzyme | 14.40 | 100.00 |

*Units = change in optical density reading per minute.
**Assuming that all the enzyme (5mg) added to the diazotised cellulose - DAB preparation coupled onto the solid successfully.

c. Inactivation of Dextranase-Active Cellulose conjugate

Having determined the enzymic activity on the cellulose-dextranase preparations, the remaining portions of the test and two control solids (i.e., in each case 80mg of solid cellulose suspended in 800µl of acetate buffer (0.2M, pH5.0)) were placed in a boiling water bath for 20 minutes. The tubes were then rapidly cooled and centrifuged. The supernatant of each solid remained unchanged in colour. An aliquot (100µ1) was removed from each stirring suspension and assayed as described in (a), samples being taken at 0 and 30 minutes. The results indicated that a very small trace of enzymic activity still remained on the "Test" solid so the suspensions now remaining (i.e. 70mg in 700µ1 of buffer) were again heated on the boiling water bath, this time for 10 minutes to give a total "heating period" of 30 minutes at 100° C. The tubes were cooled to room temperature as before and again assayed, together with a standard dextranase solution (1mg/cm³) and a "reagent blank" (0.2M acetate buffer, 200µ1), following the same method described previously (Table 19).

Table 19

Enzymic Activities on the Solid Phase Dextranase/Sigmacell Preparations (which had been inactivated by heating at 100° C) as Determined on assaying with DNS Reagent

| Sample | Enzymic Activity (Units*/mg** protein) | % Activity** (relative to soluble enzyme) |
|---|---|---|
| Control A: cellulose/enzyme | 0.00 | 0.00 |
| Control B: cellulose/DAB | 0.00 | 0.00 |
| Test: cellulose/DAB/enzyme | | |
| after 20 min. heating | 0.014 | 1.50 |
| after 30 min. heating | 0.000 | 0.00 |
| Soluble enzyme | 0.966 | 100.00 |

(*Units = change in optical density reading per minute.)
(**Assuming that all the enzyme added had coupled successfully.)

These results show complete inactivation of the active cellulose has occurred after heating of the suspension for 30 minutes in boiling water. It was observed that after heating cellulose at 100° C the character of the solid-phase was altered. The particle size of the cellulose appeared to have increased and the suspension when centrifuged did not "pack down" as it had prior to heating.

d. Re-diazotization and Coupling of Dextranase to Inactivated Cellulose

After inactivation and assay of the cellulose samples, 50 mg of each solid remained, suspended in 500µl of buffer. The suspensions were centrifuged and the supernatants removed. Diaminobenzene (0.025gms) and hydrochloric acid (1.0N, 1.0cm³) were then added to each tube and mixed with the cellulose (50mg) using a vortex stirrer. The remainder of the diazotisation/coupling procedure was then repeated precisely as carried out before but using half the quantities taken previously during the washing procedure following coupling of the enzyme to the test and control solids it was observed that much less "pink colour" leached off the test and control B solids than had washed off the first time the cellulose was coupled with diaminobenzene and dextranase.

The increased particle size of the cellulose after heating at 100° C made it difficult to "take up" the cellulose (50mg) in buffer (500µ1). It was necessary to modify the procedure followed to overcome this: the cellulose was suspended in 1cm³ of buffer and aliquots (100µ1) of this suspension were then taken for the dextranase assay. The standard and blank solutions were taken as 200µ1 aliquots as before and the method previously described again followed. The optical densities of the supernatants were determined at 570nm (Table 20).

Table 20
Enzymic Activities on the Solid Phase Dextranase/
Sigmacell Preparations (Repeat Coupling) as
Determined on Assaying with Dinitrosalicylate Reagent

| Sample | Enzymic Activity (Units*/mg** protein) | % Activity** (relative to soluble enzyme) |
|---|---|---|
| Control A: cellulose/enzyme | 0.02 | 2.42 |
| Control B: cellulose/DAB | 0.00 | 0.00 |
| Test: cellulose/DAB/enzyme | 0.16 | 16.30 |
| Soluble enzyme | 0.950 | 100.00 |

(*Units = change in optical density reading per minute.)
(**Assuming that all the enzyme (2.5mg) added to the diazotised cellulose-DAB preparation coupled onto the solid successfully).

c. Linkage of Dextranase to Cellulose using dilute enzyme solution

Diluted dextranase (0.2mg/cm$^3$, 5.0cm$^3$) was coupled to 100mg cellulose via the cellulose-diaminobenzene method described above. Two "controls" were again prepared using the same procedure but in one case omitting the diaminobenzene and the second omitting the enzyme. Washing was as previously described with one additional acetate buffer wash. The supernatants of the two diaminobenzene-treated solids remained slightly coloured, but the solids were suspended in acetate buffer (0.2M, pH5.0; 5.0cm$^3$) and the enzymic activity present on the solids determined.

Aliquots of each suspension (200μl) were incubated with substrate solution (2.5cm$^3$) at 37° C for periods of 15 and 30 minutes and assayed as above. Several additional assay blanks were prepared: a reagent blank (2.7cm$^3$ buffer), a DNS assay blank (200μl buffer, 2.5cm$^3$ substrate), and sample blanks for each of the test and control suspensions (200μl sample suspension, 2.5cm$^3$ buffer) were all prepared and treated as described as above. Two enzyme standards were also prepared: Standard 1 (200μl destranase (1mg/cm$^3$ in acetate buffer), 2.5cm$^3$ substrate) and Standard 2(100μl dextranase (1mg/cm$^3$), 2.5cm$^3$ substrate). The optical densities given by these solutions/supernatants are reported in Table 21.

Table 21
Enzymic Activities on the Solid Phase
Dextranase/Sigmacell Preparation as Determined
on Assaying with Dinitrosalicylate Reagent

| Sample | Enzymic Activity (Units*/mg** protein) | % Activity** (relative to soluble enzyme) |
|---|---|---|
| Control A: cellulose/enzyme | 0.00 | 0.00 |
| Control B: cellulose/DAB | 0.00 | 0.00 |
| Test: cellulose/DAB/enzyme | 0.35 | 37.00 |
| Soluble enzyme | 0.916 | 100.00 |

(*Units = change in optical density reading per minute.)
(**Assuming that all the enzyme (1.0mg) added to the diazotised cellulose-DAB preparation coupled onto the solid successfully.)

EXAMPLE 8 a. Linkage of Dextranase to Bioglas-1000 using concentrated enzyme solution The method of linkage followed was exactly as in Example 7(a) for the linkage of Dextranase to cellulose, replacing the "Sigmacell" with 0.10 gms of Bioglas-1000 beads. The latter were straight from the bottle. It was observed throughout the washing and centrifugation procedures that the Bioglas particles only centrifuged down with difficulty; even after thorough centrifugation at high speed supernatants were slightly cloudy owing to the presence of very fine Bioglas particles. Clearly this will lead to a gradual loss of some of the original solid and consequently the introduction of a small error into any quantitative calculations made.

Determination of Dextranase activity: The same method as was described for cullulose in 5(b) was again used, 200μl aliquots of the "test" and "control" suspensions being taken for assay. Optical densities of the supernatants were again read at 570nm against a water blank (Table 22).

Table 22
Enzymic Activities on the Solid Phase
Dextranase/Bioglas Preparations
as Determined on Assaying with DNS Reagent

| Sample | Enzymic Activity (Units*/mg** protein) | % Activity** (relative to soluble enzyme) |
|---|---|---|
| Control A: Bioglas/enzyme | 0.047 | 4.90 |
| Control B: Bioglas/DAB | 0.00 | 0.00 |
| Test: Bioglas/DAB/enzyme | 0.0.184 | 19.10 |
| Soluble enzyme | 0.960 | 100.00 |

(*Units = change in optical density reading per minute.)
(**Assuming that all the enzyme (5.0 mg) added to the diazotised bioglas-DAB preparation coupled onto the solid successfully.)

b. Inactivation of Dextranase-active Biogles-1000 conjugate

Having assayed the dextranase activity on the Bioglas support, the remainder of the suspensions (80mg Bioglas in 800 μl of acetate buffer, 0.2N, pH5.0) were heated at 100° C for twenty minutes. After cooling the suspensions to room temperature, 100μμl aliquots were removed from each tube for assay. As for the cellulose, a small trace of activity remained on the "test" solid. The suspensions were, therefore, reheated to 100° C for a further ten minutes and then assayed for dextranase activity exactly as described for the cellulose case. The results obtained are given in Table 23.

Table 23
Enzymic Activities on the Solid Phase Dextranase/Bio-
glas Preparations (which had been inactivated by heating at 100° C)
as Determined on Assaying with DNS Reagent.

| Sample | Enzyme Activity (Units*/mg** protein) | % Activity** (relative to soluble enzyme |
|---|---|---|
| Control A: | 0.00 | 0.00 |
| Control B: | 0.00 | 0.00 |
| Test: Bioglas/DAB/enzyme | | |
| after 20 min. heating | 0.006 | 0.60 |
| after 30 min. heating | 0.00 | 0.00 |
| Soluble enzyme | 0.975 | 100.00 |

(*Units = change in optical density reading per minute.)
(**Assuming that all the enzyme added had coupled successfully.)

These results indicate that the coupled enzyme is completely inactivated after heating the "test" solid at 100° C for 30 minutes. Even after only 20 minutes there is very little enzymic activity remaining on the solid.

c. Re-diazotisation and coupling of Dextranase of Inactivated Biogles-1000

The method of diazotisation and coupling of "Fresh" diaminobenzene and enzyme to the inactivated Bioglas solid was carried out exactly as described in (a) but using half the quantities given in (a) as the quantity of Bioglas treated here is 50mg of suspended inactivated Bioglas in 500 μl of buffer. After carrying out the sucrose/salt/buffer wash cyle the solid was suspended in 500μl buffer.

Determination of dextranase activity: 200 μl aliquots of each suspension were taken for assay and treated exactly as previously described. A blank and a standard sample were also assayed. Results are given in Table 24.

Table 24

Enzmic Activities on the Solid Phase Dextranase/Bioglas Preparations (Repeat Coupling) as Determined on Assaying with DNS Reagent.

| Sample | Enzmic Activity (Units*/mg** protein) | % Activity** (relative to soluble enzyme) |
|---|---|---|
| Control A: Bioglas/enzyme | 0.022 | 2.32 |
| Control B: Bioglas/DAB | 0.00 | 0.00 |
| Test: Bioglas/DAB/enzyme | 0.186 | 19.65 |
| Soluble enzyme | 0.946 | 100.00 |

(*Units = change in optical density reading per minute).
(**Assuming that all the enzyme added had coupled) (2.5 mg)

d. Linkage of Dextranase to pretreated "Bioglas 1000" Porous Glass Beads

"Bio-glas 1000" porous glass beads (120-200 mesh size) were first prepared for use following the manufacturer's instructions: eluting solution hexamethylsiloxane) was added to a quantity of the glass beads in a filter tube and the tube was then evacuated. Bubbling in the flask began indicating that air was being removed from the internal pores of the glass, thereby forcing in eluting solution. The glass was allowed to stand under vacuum for a further five minutes after bubbling had stopped. The supernatant was then decanted off and the solid left under vacuum for another fifteen minutes before being left to dry in the oven. An hour and a half later the beads were removed from the oven and cooled. They were then linked to dextranase exactly as described in (a) using 0.5cm$^3$ of a 10mg/cm$^3$ solution of of dextranase. The results are given in Table 25.

Table 25

Enzymic Activities on the Solid Phase Dextranase/Bioglas (Pretreated) Preparations as Determined on Assaying with DNS Reagent.

| Sample | Units of Enzymic Activity Detected | % Activity** (relative to soluble enzyme) |
|---|---|---|
| Control A: Bioglas/enzyme | 0.19 | 3.7 |
| Control B: Bioglas/DAB | 0.00 | 0.0 |
| Test: Bioglas/DAB/enzyme | 1.75 | 33.3 |
| Soluble enzyme | 5.10 | 100.0 |

(**Assuming that all the enzyme (5.0 mg) added to the diazotised Bioglas-DAB preparation coupled onto the solid.)

EXAMPLE 9 a. Linkage of Dextranase to Celite

Diazotisation of the diaminobenzene/celite suspension and linkage of the enzyme to the treated solid was carried out exactly as in Example 7(a) replacing the Sigmace11 with 0.10 gms of Celite. It was observed that "Control B" lost a considerable "amount" of colour (deep pink) whenever it was washed with sucrose/salt-/buffer, but after several washings with acetate buffer alone the supernatant remained quite clear. The "test" solid when washed in the normal manner produced no excess pink colouring observable in any of the supernatants. The solids were finally suspended in acetate buffer (0.2M, pH5.0, 1cm$^3$) as before.

Determination of Dextranse activity: 200 μl aliquots of the "test" and "control" suspensions were taken for assay in exactly the same manner as described previously. Reagent blank and soluble enzyme samples were also assayed as before. Optical densities were determined at 570 nm against a water blank (Table 26).

Table 26

Enzymic Activities on the Solid Phase Dextranase/Celite Preparation as Determined on Assaying with DNS Reagent.

| Sample | Enzymic Activity (Units*/mg** protein) | % Activity** (relative to soluble enzyme) |
|---|---|---|
| Control A: celite/enzyme | 0.00 | 0.00 |
| Control B: celite/DAB | Optical density decreased with increasing length of incubation. | |
| Test: celite/DAB/enzyme | 0.207 | 21.80 |
| Soluble enzyme | 0.947 | 100.00 |

(*Units = change in optical density reading per minute)
(**Assuming that all the enzyme (5.0 mg) added to the diazotised celite-DAB preparation coupled onto the solid)

That the enzyme somehow aids in "fixing" the diaminobenzene molecules to the solid support is suggested by the observed behaviour of Control B here: when no enzyme is coupled to the diazotised solid the red color "on" the Celite is readily released during the exhaustive washing procedure. The particle size of the Control B "Celite" would also appear to be smaller than that for the test as it is more difficult to centrifuge down the Control B suspension.

b. Inactivation of Dextranase-active Celite

The Celite -DAB control suspension ("B") was not included in further experiments owing to the interference caused in the DNS assay by the excessive "leaching-off" of pink colour from the solid. The remainder of the Control A and Test suspensions (80mg of solid in 800 μl acetate buffer (0.25H, pH5.0)) were each heated on a boiling water bath for 20 minutes and then cooled to room temperature. After centrifuging it was observed that the "test" supernatant had increased in colour slightly. The supernatants were removed and the solids resuspended in acetate buffer (0.2N,pH5.0, 800 μl). Aliquots of each stirred suspension were removed and taken for assay for dextranase activity together with a standard dextranase solution (1mg/cm$^3$, 200 μl) and a buffer blank (200 μl). Determination of Dextranase activity: the method previously described was again followed (results given in Table 27).

Table 27

Enzymic Activities on the Solid Phase Dextranase/Celite Preparations (which had been heated for 20 minutes at 100° C to inactivate the enzyme) as Determined On Assaying with DNS Reagent.

| Sample | Enzymic Activity (Units*/mg** protein) | % Activity** (relative to soluble enzyme) |
|---|---|---|
| Control A: celite/enzyme | 0.00 | 0.00 |
| Test: celite/DAB/enzyme | 0.00 | 0.00 |
| Soluble enzyme | 0.947 | 100.00 |

(*Units = change in optical density reading per minute)
(**Assuming that all the enzyme added had coupled)

These results indicate that destruction of all enzymic activity has occurred after heating at 100° C for 20 minutes.

c. Re-diazotisation and Coupling of Dextranase to Celite Following Inactivation of Previous Active Solid-Phase Dextranase Preparation After carrying out the assays previously described, 60mg of each solid remained (each suspended in 600 μl of acetate buffer). The suspensions (Control A and Test) were centrifuged and the supernatants removed. The solid (60mg) was then in each case diazotised as before taking suitable quantities of all reagents. For each of the two solids 30 mgs of diaminobenzene were added, and the quantity of dextranase taken was reduced from 5.0 mgs to 3.0mgs in each case. After carrying out the washing procedure previously described the solids were suspended in acetate buffer (0.2M, pH5.0, 600μ1).

Determination of Deztranase activity: 200 μ1 aliquots of each suspension were taken for the assay, which was carried out exactly as before (Results, Table 28).

Table 28

Enzymic Activities on the Solid Phase Dextranase/Celite Preparations (Repeat Coupling) as Determined on Assaying with DNS Reagent.

| Sample | Enzymic Activity (Units*/mg** protein) | % Activity** (relative to soluble enzyme |
|---|---|---|
| Control A: celite/enzyme | 0.00 | 0.00 |
| Test: celite/DAB/enzyme | 0.131 | 13.50 |
| Soluble enzyme | 0.974 | 100.00 |

(*Units = change in optical density reading per minute)
(**Assuming that all the enzyme added (2.5 mg) had coupled)

EXAMPLE 10 a. Linkage of Dextranase to Nylon

The source of the nylon used here was a pair of nylon tights which had been thoroughly bolied to remove most of the dye. Eight small squares of nylon, as similar in size as was possible, were cut and weighed. Four squares (average weight: 6.1mgs) were then put into each of two tubes to give a total weight of nylon of about 24.4mgs per tube. One tube was used as the test sample, the other providing a control.

Diazotisation of the nylon was carried out following the method previously described. Diaminobenzene (12.5mgs) was added to nylon (24.2mgs) and hydrochloric acid (1.0N, 1.0cm³) was then added. On addition of acid to the "Control A" tube (containing no diaminobenzene it was observed that the solution became yellow and the nylon solid changed in colour from beige to a yellow/beige colour. The "Test" nylon, with diaminobenzene present, did not change colour, and neither did the Test supernatant. On addition of sodium nitrite (2% w/v, 1.0cm³) the yellow colour of the "Control" nylon changed to a pale pink/beige and the yellow solution became colourless. The "Test" nylon and its supernatant changed in colour to wine-red.

Each sample of nylon was then washed three times with acetate buffer as before. It was not necessary to contrifuge between washes: the wash solutions were simply removed using a Pasteur pipette. The red colour of the "Test" solution was easily removed on washing to leave the red nylon squares in a colourless solution of buffer. The pink/beige colour of the control solid remained unchanged, and each wash solution was colourless. Enzyme (1mg/cm³, 1cm³) was then added to each tube and the suspensions stirred at 4° C for 18 hours. β-naphthol (saturated in saturated sodium acetae, 1.0cm³) was added to each tube the following morning and the suspensions were stirred for 30 minutes. The normal exhaustive washing procedure was then carrued out and the samples finally suspended in buffer (1.0cm³). Two squares of nylon were removed from each of the test and control tubes and suspended in acetate buffer (0.2M, pH5.0, 200 μ1) to carrying out the dextranase assay.

Determination of Dextranase activity: the assay was performed as described previously except that none of the 'solid suspension' could be removed at each time during incubation: instead an aliquot of the substrate/buffer solution was removed each time. A blank and standard dextranase solution were prepared and assayed in the normal manner. Results are given in Table 29.

Table 29

Enzymic Activities on the Solid Phase Dextanase/Nylon Preparations as Determined on Assaying with DNS Reagent, both before and after heating.

| Sample | % Activity** (relative to soluble enzyme) |
|---|---|
| Control: Nylon/enzyme | 0.0 |
| after 20 mins at 100° | 0.0 |
| Test: Nylon/DAR/enzyme | 3.9 |
| after 20 mins at 100° | 0.0 |
| Soluble enzyme | 100.0 |

(**Assuming that all the enzyme (1.0 mg) added to the diazotised nylon-DAB preparation coupled onto the solid.)

b. Inactivation of Dextranase-Active Nylon

Each remaining sample of nylon (i.e., 2 square each of the "test" and "control" samples) were heated on a boiling water bath for twenty minutes. No colour was observed to have "leaked off" the solids into solution after heating and cooling to room temperature.

Determination of Dextranase-activity: the two inactivated nylon samples were assayed exactly as described in (a). (Results, Table 20 ).

No increase in optional density was observed for the heated "Test" sample: The enzymic activity on the nylon had been destroyed totally after heating for 20 minutes.

c. Re-diazotisation and Coupling of Dextranase to Inactivated Nylon

The inactivated "test" and "Control A" samples of nylon were thoroughly washed with buffer (4 × 5.0cm³) to remove any substrate solution adhering to the squares after the dextranase assay. The diazotisation and coupling procedure was then followed exactly as before but using in all cases half the original quantities of reagents. The nylon samples were again very easily washed free of all red colour from the diaminobenzone. It was observed that on re-diazotisation of the "test" sample the color of the nylon was less "uniform" than it had been the first time, i.e., some regions were more deeply stained (red) than others. Following a complete washing cycle, both "test" and "control" nylon squares were suspended in acetate buffer (0.2M, pH5.0, 200 μ1) preparatory to assaying for enzymic activity.

Determination of Dextranase-activity: the assay was carried out exactly as described in (a). Results are given in Table 30.

Table 30

Enzymic Activities on the Solid Phase Dextranase/Nylon Preparations (Repeat Coupling) as Determined on Assaying with DNS Reagent.

| Sample | % Activity** (relative to soluble enzyme) |
|---|---|
| Control: Nylon/enzyme | 0.00 |
| Test: Nylon/enzyme DAB | 2.4 |
| Soluble enzyme | 100.00 |

(**Assuming that all the enzyme (0.5 mg) added to the diazotised nylon-DAB preparation coupled onto the solid.)

EXAMPLE 11 a. Linkage of Dextranase to Neosyl using concentrated enzyme solution

The coupling of dextranase to Reosyl was carried out exactly as in Example 7 (a) replacing the Sigmacell with Neosyl. Some difficulty was encountered during the washing cycles as the finer particles of Reosyl were not completely "centrifuged down" after the usual centrifugation time (2 –3 minutes). This problem was particularly noticeable with the Control A suspension (i.e., without diaminobenzene). The difficulty was overcome by increasing the centrifugation time to 5–6 minutes. The solids were finally suspended in acetate buffer (0.2M,pH5.0, 1.0cm$^3$) and then assayed for enzymic activity.

Determination of dextranase-activity on the solids: 200 μl aliquots of the suspensions were taken for assay following the same method used previously. Results are given in Table 32.

Table 32

Enzymic Activities on the Solid Phase Dextranase/Neosyl Preparations as Determined on Assaying with DNS Reagent.

| Sample | Enzymic Activity (Units*/mg protein) | % Activity (relative to soluble enzyme) |
|---|---|---|
| Control: neosyl/enzyme | 0.010 | 0.10 |
| Test: Neosyl/DAB/enzyme | 0.273 | 27.95 |
| Soluble enzyme | 0.974 | 100.00 |

(*Units - change in optical density reading per minute).
(**Assuming that all the enzyme (5.0 mg) added coupled onto the solid).

b. Inactivation of Dextranase-Active Neosyl

Two aliquots (500 μl each) were removed from the stirred suspensions remaining and were heated in stopped tubes on a boiling water bath for 20 minutes. They were then cooled to room temperature and centrifuged. The supernatant of the "test" sample was a fairly deep orange/red in colour. Both the test and control solids were, therefore, subjected to two washes in acetate buffer before being finally suspended in acetate buffer (500 μl). Aliquots (200 μl) from the suspensions were then taken for assay of enzymic activity.

Determination of dextrananase-activity on the solids: 200 μl aliquots of the suspensions were taken for assay exactly as previously described. Results are given in Table 33.

Table 33

Enzymic Activities on the Solid Phase Dextranase/Neosyl Preparations (which had been inactivated by heating at 100° C for 20 minutes) as Determined on Assaying with DNS Reagent.

| Sample | Enzymic Activity (Units*/mg protein) | % Activity (relative to soluble enzyme) |
|---|---|---|
| Control: Neosyl/enzyme | 0.00 | 0.00 |
| Test: Neosyl/DAB/enzyme | 0.00 | 0.00 |

(*Units as previously defined).

These results indicate that all activity on the solid had been destroyed by this treatment.

(N.B. The suspensions containing diaminobenzene produce a high optical density reading even before incubation at 37° C both when active and inactive).

c. Re-diazotisation and Coupling of Dextranase to Inactivated Neosyl

The remaining solid (30mg suspended in 300 μl of buffer) was diazotised and linked to dextranase via diaminobenzene exactly as previously described, using suitably sealed-down quantities of all reagents. The re-coupled "Test" Neosyl seemed to "centrifuge down" more easily than it had the first time, but considerable difficulty was still encountered in the centrifugation of the control without diaminobenzene.

Determination of Dextranase Activity: 200 μl aliquots of the suspensions were taken for assay in the usual manner. Results are given in Table 34.

Table 34

Enzymic Activities on the Solid Phase Dextranase/Neosyl Preparations (Repeat Coupling) as Determined on Assaying with DNS Reagent.

| Sample | Enzymic Activity (Units*/mg protein) | % Activity** (relative to soluble enzyme) |
|---|---|---|
| Control: Neosyl/enzyme | 0.006 | 0.60 |
| Test: Neosyl/DAB/enzyme | 0.191 | 19.45 |
| Soluble enzyme | 0.980 | 100.00 |

(*;** as previously defined).

EXAMPLE 12

Cellex-CM (Bio-Rad Cation Exchange Cellulose, Exchange capacity = 0.69meq/g) is highly purified cellulose powder containing carboxy-methyl ion-exchange groups in the sodium form. The coupling procedure was carried out exactly as in Example 7 (a) replacing cellulose with Cellex-CM. A slight alteration was made in that only 500 μl β-naphthol (saturated sodium acetate) was added to the stirred suspension. The normal cycle of washings was performed on the test and control Cellex-CM samples. The "test" supernatant was still definitely pinkish in colour on completion of the cycle. The "Cellex-CM" test solid wash, therefore, washed a further 20 times before suspending in 0.2M acetate buffer pH5.0, 4.5cm$^3$.

Four tubes were prepared for assay:
A. 1000 μl buffer.
B. 500 μl enzyme (1mg/cm$^3$), 500 μl buffer.
C. 500 μl "control" Cellex-CM, 500 μl buffer.
D. 500 μl "test" Cellex-CM, 500 μl buffer.

The assay was then carried out as described for dextranase previously. Much red colour "leaked-off" during the incubation: it was in fact impossible to obtain any optical density readings for the "test" suspension against a DNS-buffer blank. The readings against a "test" supernatant blank are given in Table 35.

Table 35

Enzymic Activities on the Solid Phase Dextranase/Cellex-CM Preparations as Determined on Assaying with DNS Reagent.

| Sample | Units of Enzymic Activity Detected | % Activity (relative to soluble enzyme) |
|---|---|---|
| Control: Cellex-CM/enzyme | 0.100 | 1.95 |
| Test: Cellex-CM/DAB/enzyme | 0.360 | 7.16 |
| Soluble enzyme | 5.10 | 100.00 |

(**Assuming that all the enzyme (5.0 mg) added coupled to the solid).

EXAMPLE 13 a. Linkage of Dextranase to DEAE Cellulose

The diethylaminoethyl cellulose used here was Whatman's "Column Chromedia Microgranular DE32 Standard Cellulose", i.e., an Anion-exchange Cellulose, manufactured as the free base (mean small-ion capacity = 1.0meq/gm drv). The coupling procedure was carried out exactly as described in Example 7(a). 2.00m$^3$ of β-naphthol was again added to each tube after the coupling. It was observed that the DEAE-cellulose washed extremely well: very little red colour came off the "test" solid even during the sucrose/salt/buffer washes. Some difficulty was encountered initially with the "control" solid: even after 20 minute-long centrifugation the solid did not "settle" fully and the supernatant remained turbid. No such problem arose with the "test" sample.

Determination of enzymic activity: the dextranase activity on the "test" sample was assayed exactly as previously described. A standard enzyme solution (0.2mg/cm$^3$) was assayed at the same time. Results are given in Table 36.

Table 36
Enzymic Activities on the Solid Phase Dextranase/
DEAE Cellulose Preparations as
Determined on Assaying with DNS Reagent.

| Sample | Units of Enzymic Activity Detected | % Activity** (relative to soluble enzyme) |
| --- | --- | --- |
| Control: DEAE/enzyme | 0.010 | 0.30 |
| Test: DEAE/DAB/enzyme | 1.75 | 34.3 |
| Soluble enzyme | 5.10 | 100.00 |

(**Assuming that all the enzyme added coupled to the solid.)

b. Re-Use Properties of DEAE-Cellulose/Dextranase Preparation

A sample of each of the previously prepared "test" and "control" suspensions (DEAE-cellulose/dextranase) was taken and centrifuged. The supernatant was then removed and discarded, to leave about 20mg of cellulose in each tube. To this at known time was added 5.0cm$^3$ of dextran solution. The suspensions were stirred on a vortex stirrer, centrifuged for one minute and a "zero-time" sample then taken and immediately transferred to a tube containing an equal (1.0cm$^3$) volume of DNS reagent. After 10 minutes the tubes were removed from the water bath and the same procedure repeated. The slight difference in concentration owing to the removal of the zero-time sample should not adversely affect the results here. Using this method, the samples taken were incubated with dextran and assayed from incubation 2 to 5. The results are given in Table 37.

Table 37
Enzymic Activities on the Solid Phase Dextranase/
DEAE-Cellulose samples after
Repeated Incubation with Dextran

| Assay | % Original Activity |
| --- | --- |
| First | 100 |
| Second | 74 |
| Third | 76 |
| Fourth | 71 |
| Fifth | 69 |

EXAMPLE 14

Linkage of Dextranase to "Biogel P-6"

Biogel P-6 (50-150 mesh) is a copolymer of acrylamide and methylenebisacrylamide and is manufactured in the form of spherical beads especially prepared for molecular sieve chromatography. 0.10gm. Aliquots of the Biogel beads in 7.0cm$^3$ water were stirred four hours to allow the beads to swell. The suspensions were then centrifuged and the supernatants removed. The coupling procedure was the same as that in Example 7(a). Washings with cold acetate buffer were carried out in the normal manner: both "test" supernatants remained strongly red-orange in colour even after the three washes (normally sufficient to remove almost all the red dye in solution). Enzyme was nevertheless added to each tube and the suspensions left to stir overnight at 4° C. The following day, after annealing the solids with β-naphthol, the usual exhaustive washing procedure was carried out, but even after having completed all the acetate buffer washes the P-6 supernatant was a light pink in colour. The P-6 solid was, therefore, subjected to 40 washes before finally being suspended in buffer (0.2M, pH5.0, 5.0cm$^3$). Even the fortieth wash supernatant was still slightly coloured.

Four tubes were prepared for assay:

A. 500 μl Control Biogel P-6, 500 μl acetate buffer.
B. 500 μl Test Biogel P-6, 500 μl acetate buffer.
C. 250 μl soluble dextranase (1mg/cm$^3$), 750 μl acetate buffer.
D. 1000 μl acetate buffer ("reagent blank").

To each tube at known time was added 5.0cm$^3$ of dextran solution. Immediately after addition of dextran and agitation of the suspension on a vortex stirrer, 1.0cm$^3$ aliquots were taken and pipetted into equal (1.0cm$^3$) volumes of DNS reagent contained in small test tubes. The contents of these tubes were then immediately mixed using a vortex stirrer. Samples were similarly taken from each incubating suspension at 5-minute intervals, a total of five samples being taken from each. When all the samples had been taken the tubes containing solid-phase samples were centrifuged for two minutes. This was done in part to determine whether any of the "red" colour of the "test" solid had "come-off" into solution during the incubation with dextran or on contact with DNS. Usually a sample of one of the supernatants was taken and "set-aside" without development by heating to 100° C: by reading the optical density of this sample along with those of the samples developed by heating to 100° C a more quantitative estimate of the extent of "leaching-off" of the red colour may be made.

In addition three "assay tubes" were prepared and developed together with the twenty samples described above:

I. 1.0cm$^3$ buffer, 1.0cm$^3$ DNS (DNS-Water Assay Blank).
II. 100 μl glucose (2mg/cm$^3$), 900 μl buffer, 1.0 cm$^3$ DNS.
III. 200 μl glucose (2mg/cm$^3$), 800 μl buffer, 1.0cm$^3$ DNS.

The tubes were then heated at 100° C in a boiling water bath for ten minutes, after which they were removed and immediately cooled in an ice-bath. Optical densities were then determined at 520nm against the DNS-water assay blank using a Unican SP-500 Spectrophotometer (Table 38).

Table 38

Enzymic Activities on the Solid Phase Biogel P-6/
Dextranase Preparations as Determined
on Assaying with DNS Reagent.

| Sample | Units of Enzyme Activity Detected | % Activity** (relative to soluble enzyme) |
|---|---|---|
| Control: Biogel P-6/enzyme | 0.05 | 0.98 |
| Test: Biogel P-6/DAB/enzyme | 0.49 | 9.6 |
| Soluble enzyme | 5.10 | 100.00 |

(**Assuming that all the enzyme added coupled to the solid)

EXAMPLE 15

The coupling of α-amylase to "Sigmacell" cellulose was carried out as in Example 7(a) except for these modifications; after dialysing the crude enzyme against distilled water for twenty-four hours, a Lowry Assay was carried out: the enzyme strength (using albumin standards) was found to be approximately 8.4mg Protein/$cm^3$. A solution of 4.2mg protein/$cm^3$ was used for the coupling: 2.5$cm^3$ of dialysed enzyme was diluted to 5.0$cm^3$ with phosphate buffer (0.03M, pH6.9). To each of the "Test" and "Control" solids was added 1.0$cm^3$ of the enzyme solution and coupled at this pH. After stirring overnight β-naphthol was added and the solids then washed: after twenty-five washings (the last fifteen being with buffer only) it was decided to attempt to carry out an assay even though the supernatant was still faintly pinkish-yellow in colour. The solids were, therefore, suspended in buffer (0.03M, pH6.9, 5.0$cm^3$).

α-Amylase activity was determined by measuring the initial rate of hydrolysis at room temperature of a solution of soluble starch (1%) in phosphate buffer (0.02M, pH6.9). The rate of formation of reducing sugar was determined by assaying aliquots of the degests with dinitrosalicylate reagent (0.10gms 3,5-dinitrosalicylic acid, 20$cm^3$ 2.0N NaOH, 50$cm^3$ water, 30gms sodium potassium tartrate, dissolved and then made-up to 100$cm^3$). Four tubes were prepared for assay:
"Test: 0.5$cm^3$ cellulose-DAE-enzyme suspension, 0.5$cm^3$ buffer.
"Control": 0.5$cm^3$ cellulose-enzyme suspension, 0.5$cm^3$ buffer.
Soluble enzyme: 0.5$cm^3$ enzyme solution(0.0084mg/$cm^3$), 0.5$cm^3$ buffer.
Reagent blank: 1.0$cm^3$ buffer.
To each tube at known time was added 5.0$cm^3$ of soluble starch solution. Immediately after addition of starch and agitation of the suspension on a vortex stirrer, 1.0$cm^3$ aliquots were taken and pipetted into equal (1.0$cm^3$) volumes of dinitrosalicylate (DNS) reagent contained in small test tubes. The contents of these tubes too were then immediately well-mixed using a vortex stirrer. Samples were similarly taken from each incubating suspension after five minute intervals, a total of five samples being taken from each. When all the samples had been taken the tubes containing solid-phase samples were centrifuged for two minutes. This was done in part to determine whether the red colour of the "Test" solid had "come off" into the solution despite the thorough washing procedure carried out. It was found that although the suspensions appeared to be red in colour, after centrifuging the supernatant visually appeared to be the same colour as all the other solutions (i.e., yellow). In addition three "assay tubes" were prepared and developed together with the twenty samples described above:

A. 1.0$cm^3$ water, 1.0$cm^3$ DNS (i.e. DNS-Water Assay Blank).
B. 200 μl maltose (2mg/$cm^3$), 800 μl water, 1.0$cm^3$ DNS.
C. 100 μl maltose (2mg/$cm^3$), 900 μl water, 1.0$cm^3$ DNS.

The tubes were then heated at 100° C in a boiling water bath for five minutes, after which they were removed and immediately cooled in an ice-bath. Optical densities were then read at 520nm on the Unican SP-500 Spectrophotometer (Table 39).

Table 39

Enzymic Activities on the Solid Phase α-Amylase/Sigmacell Preparations as Determined on assaying with DNS Reagent.

| Sample | Units of Enzymic Activity detected | % Activity** (relative to soluble enzyme) |
|---|---|---|
| Control: Cellulose/enzyme | 3 | 1 |
| Test: Cellulose/DAB/enzyme | 40 | 13 |
| Soluble enzyme | 307 | 100 |

(**Assuming all the enzyme (4.2 mg) added to the diazotised cellulose-DAB preparation coupled successfully.)

EXAMPLE 16

The coupling of glucoamylase to cellulose was again carried out as in Example 7(a), except for these modifications. The crude glucoamylase was dialysed against distilled water for twenty-four hours: the dialysed enzyme contained approximately 20mg protein/$cm^3$. A solution of approximately 4mg protein/$cm^3$ was used for the coupling: 1.0$cm^3$ of dialysed enzyme was diluted to 5.0$cm^3$ with phosphate buffer, pH8.0, and 1.0$cm^3$ of this solution coupled at this pH to each of the "Test" and "Control" solids. The coupled solids were washed with acetate buffer, pH4; thirty-seven washes were carried out before the supernatant was clear enough for a reasonable attempt to assay the enzymic activity to be made. The solids were suspended in acetate buffer (0.2M, pH 4.0, 5.0 $cm^3$).

Four tubes were prepared, each containing 4.5$cm^3$ of starch solution (1% in acetate buffer, 0.2M, pH4.5). To each tube was added at known time 0.5$cm^3$ of "Test" suspension, "Control" suspension, soluble enzyme, or buffer, and the tubes were then incubated at 37° C. Aliquots were removed at "zero time" and then at five minute intervals for twenty minutes: aliquots of 0.10$cm^3$ were taken and transferred to previously prepared tubes (cooling in an ice-bath) containing 2.9$cm^3$ of freshly prepared o-dianisidine reagent (10mg glucose oxidase, 5mg peroxidase, 1.0$cm^3$ o-dianisidine solution, made up to 100$cm^3$ with Tris buffer, pH7.0). When all the aliquots had been taken the tubes were incubated at 37° C for an hour and their optical densities then read at 450nm. Unfortunately, it was found that the cellulose solid absorbed some of the colour from the solutions, to such an extent that the "Control" cellulose solids in the assay tubes changed from white to pinky-brown. It was, therefore, necessary to modify the assay slightly to overcome this difficulty. This was done by taking six stoppered test tubes and putting into each 0.10$cm^3$ of solid-phase suspension. To each tube at known time was added 0.7$cm^3$ of starch solution, and incubation continued at 37° C. Immediately after addition of starch to the sixth test tube, all tubes were removed from the water bath, cooled for 30 seconds and centrifuged at high speed for one minute. Then starting with the sixth tube, 0.10$cm^3$ aliquotes were rapidly removed from each tube in turn and transferred to previously prepared tubes containing 2.9cm³ of o-dianisidine solution. All tubes were then incubated at 37° C for an hour, as before, and their optical densities then determined at 450nm. Using this method, the results obtained were quite satisfactory (Table 40). (The concentration of the free enzyme solution employed was 1.0 g/cm³.)

Table 40.

Enzymic Activities on the Solid Phase Glucoamylase/Cellulose Preparations as Determined on Assaying with o-dianisidine reagent.

| Sample | Units of Enzymic Activity detected | % Activity** (relative to soluble enzyme) |
|---|---|---|
| Control:cellulose/enzyme | 0.97 | 2 |
| Test:cellulose/DAB/enzyme | 5.31 | 12 |
| Soluble enzyme | 44.40 | 100 |

(**As defined for amylase.)

b. The Effect of Washing with DMSO on the Activity of Solid-Phase Glucoamylase It was decided to determine whether washing with an organic solvent would effect removal of the excess red colour faster but have no ill-effects on the activity of the enzyme. Dimethyl sulphoxide was chosen as a suitable solvent and a 50% solution prepared using DMSO (previously dry and distilled) in acetate buffer, pH8.0, 1.0cm³ of the previously prepared solid-phase glucoamylase "test" suspension was taken into each of two tubes and the same done with the "control" suspension. The tubes were then centrifuged and the supernatants removed. One of the "test" and one of the "control" suspensions were then treated with 5.0cm³ of the DMSO solution and left to stir for an hour at room temperature. 5.06m³ of acetate buffer was added to each of the other two tubes and they too were allowed to stir for an hour, after which all four suspensions were centrifuged and their supernatants removed. Each solid was resuspended in acetate buffer (0.2H, pH5.0, 1.0cm³). The four suspensions were then assayed for enzymic activity exactly as before, using the o-dianisidine method (Results, Table 41).

Table 41

Enzymic Activities on the DMSO and Buffer Washed Samples of the Glucoamylase/Cellulose Preparations as Determined on Assaying with o-dianisidine.

| Sample | Enzymic Activity (Units */mg protein) | % Activity** (relative to soluble enzyme) |
|---|---|---|
| Control-DMSO washed | 0.00 | 0.00 |
| Control-Buffer washed | 0.00 | 0.00 |
| Test-DMSO washed | 0.30 | 8.80 |
| Test-Buffer washed | 0.33 | 9.70 |

(*,** as defined above.)

It is clear that the DMSO treatment has very little effect on the activity of the enzyme although it is much more effective at removing the colour that is "neat" acetate buffer.

EXAMPLE 17

Catalase was coupled to cellulose using the coupling and washing procedure described in Example 7(a). 2.5Mg of catalase in 500μl of buffer was added to each of the "Test" and "Control" solids. An additional "colour control" was prepared here: the same coupling procedure was used as for the "Test" cellulose, but no enzyme was added after the diazotisation of the diaminobenzene. It was observed that the "test" sample gave darker supernatant washings than the cellulose-DAB control when washed with either buffer or sucrose-salt-buffer. After four final buffer washes (acetate buffer, pH5.0), each sample was washed with 0.05M phosphate buffer, pH7.0 (4 × 5.0cm³) in preparation for assay of enzymic activity.

A standard enzyme solution (5μg/cm³ in phosphate buffer, 0.05M, pH7.0, 400μl) was treated with the hydrogen peroxide substrate (30% approximately - 250μl diluted to 25cm³ with phosphate buffer; 200μl). This gave an initial absorbance of 1.057 at 240nm, measured against buffer and at the concentration present for each assay. A sample of standard enzyme (400μl) plus buffer (200μl) gave an absorbance of 0.031 at 240nm (read against buffer). Thus the zero time absorbance must be 1.088 for the enzyme standard. On addition of the substrate at "zero time" the solution was mixed at room temperature and, after transferring an aliquot to a microcell, readings of the optical density were made at thirty second intervals as the absorbance decreased. Readings were made over a period of twelve minutes.

For the assays of the solid-phase enzyme samples, 50μl aliquots of the suspensions were transferred into small test tubes containing buffer (350μl). One tube was used for each time interval to be tested, both for the "test" and the "control" samples. Each sample was then treated with substrate (200μl), the time of addition of substrate being recorded as zero time. For each timed assay (either 1, 2, 3 or 4 minutes) a new sample of suspended cellulose was treated with substrate. Thus for a typical determination the substrate was added as the stopwatch was started. The solution was then stirred on a vortex stirrer and the tube was then centrifuged. An aliquot (400μl) of the supernatant was then transferred to the microcell and the reading at 240nm and known time recorded. This procedure was repeated for each of the test and control suspensions after incubation periods of 1, 2, 3 and 4 minutes (Table 33).

Table 42

Enzymic Activities on the Catalase/Cellulose Preparations as Determined after Assaying with Hydrogen Peroxide.

| Sample | Enzymic Activity (Units*/mg protein) | % Activity** (relative to soluble enzyme) |
|---|---|---|
| Control:cellulose/enzyme | 0.02 | 0.04 |
| Test:cellulose/DAB/enzyme | 10.90 | 20.00 |
| Soluble enzyme | 54.50 | 100.00 |

(*,** as previously defined.)

EXAMPLE 18

Glucose oxidase was coupled to cellulose using the procedure in Example 7(a) with these modifications. Three tubes were prepared as before, a "test", a "control" and a "colour control". Washing and coupling of the solid was, however, carried out with phosphate buffer, pH6.0. It was found that the supernatants were clear by the end of the sucrose/saltbuffer cycle of washes: this was attributed to the use of a concentrated solution of enzyme, 0.5cm³ of a 10mg/cm³ solution of glucose oxidase (crystalline, Boehringer) having been added to each of the first two tubes.

The ABTS (ammonium salt of 2,2'-azino-di(3-ethylbenzy(thiazolinsulphonic acid-6)) method of assay of glucose oxidase was chosen as being the most convenient, and the procedure followed was very similar to that developed for the o-dianisidine assay of Glucoamylase. Four tubes were prepared, each containing 2.5cm³ ABTS solution (500mg/l in phosphate buffer, 0.1M, pH7.0), 500μl glucose (10% in phosphate buffer, pH7.0) and 200μl peroxidase (0.2mg/cm³). The tubes (all equipped with magnetic stirrer bars - as for all assays reported here) were then allowed to equilibrate briefly, with stirring, in a water bath at 37° C. At known times 100μl aliquots of the sample to be assayed were added to the tubes, which were then vigorously agitated on the vortex stirrer before being replaced in the bath. Immediately after addition of the 100μl sample aliquot to the fourth tube, all four tubes were removed from the water bath and centrifuged at high speed for one minute. The supernatant was then removed from each tube and transferred to a clean tube. The optical densities of the supernatants were then read at 415nm against a water blank. Using this method only one enzyme solution/suspension can be assayed at a time, but it is possible to imitate very closely the procedure followed with the first sample assayed when performing later assays, so any error involved in not performing the assays "side-by-side" is probably minimal. The free enzyme solution used was of strength 0.1mg/cm³. For the solid phase "test" it was found that the absorbances when assaying 0.10cm³ of the "test" suspension (i.e., 100mg cellulose solid in 5.0cm³ phosphate buffer) were too high to read: an aliquot (0.100cm³) of each solid phase suspension was, therefore, diluted by ten (i.e., to 10.0cm³ with phosphate buffer) and the new more-dilute suspensions (100μl) taken for assay. The results (Table 34) obtained using this assay were found to be very satisfactory and corresponded to 17.7% enzyme activity on the solid of that applied.

Table 43

Enzymic Activities on the Glucose Oxidase/Cellulose Preparations as Determined after Assaying with ammonium salt of 2,2'-azino-di(3-ethyl benzylthiazolin-sulphonic acid-6)(ABTS).

| Sample | Units of Enzymic Activity Detected | % Activity** (relative to soluble enzyme) |
|---|---|---|
| Control:Cellulose/enzyme | 16 | 2.4 |
| Control:Cellulose/DAB | Optical Density decreases with time. | |
| Test:Cellulose/DAB/enzyme | 117 | 17.7 |
| Soluble enzyme | 660 | 100.0 |

(** as defined above.)

EXAMPLE 19

Linkage of Glucose Oxidase to "Bioglas 1000" Porous Glass Beads

The preparation of the solid-phase enzyme was carried out exactly as previously described for the linkage of dextranase to Porous Glass Beads in Example 9(a) again using 0.10 gms glass beads, 0.05gms diaminobenzene and 0.5cm³ of enzyme solution (10gm/cm³). Phosphate buffer, pH6.0, was, however, used throughout the coupling and washing procedures.

The ABTS method of assay was again employed, following the procedure previously described in Example 18. The results obtained (Table 44) are quite satisfactory and indicate that the "solid phase test" now carries a resonable amount of enzyme, though somewhat less than did the cellulose-DAB- glucose oxidase "test".

Table 44

Enzymic Activities on the Glucose Oxidase/Bioglas Preparations as Determined after Assaying with ABTS.

| Sample | Units of Enzymic Activity Detected | % Activity** (relative to soluble enzyme) |
|---|---|---|
| Control:Bioglas/enzyme | 10 | 1.5 |
| Test:Bioglas/DAB/enzyme | 69 | 10.5 |
| Soluble enzyme | 660 | 100.0 |

(** As defined above.)

EXAMPLE 20

Peroxidase (2.5mg in 500 μl) of acetate buffer, 0.2M, pH5.0) was coupled to cellulose-diaminobenzene as in Example 5(a) and then washed. After the initial five cycles of washing with acetate buffer and sucrosesalt solution, the cellulose sample and controls (cellulose-enzyme and cellulose-DAB) were washed with acetate buffer (0.2M, pH5.0 4 × 5cm³), followed finally by washings with phosphate buffer (0.1M, ph7.0, 4 × 5cm³) to prepare the solids for assay of peroxidase activity.

Determination of Peroxidase Activity: A modified version of the ABTS assay previously described for Glucose Oxidase was used to assay for peroxidase. The enzymic activity of a standard solution was first determined. An aliquot of standard peroxidase solution (1mg/cm³ in 0.1M phosphate buffer, pH7.0, 25μl) was added to a solution containing ABTS reagent (0.5mg/cm³ in 0.1M phosphate buffer, pH7.0, 2.5cm³) and hydrogen peroxide (substrate) solution (approximately 0.003% in water, 500μl), and zero time was noted. The solution was thoroughly mixed and its absorbance at 415nm determined at intervals of 5 minutes for 30 minutes, reading against buffer on the Unicam S.P. 500 Spectrophotometer. The absorbance of the blank solution (containing no enzyme but instead an aliquot of buffer (25μl)) was read and this value taken as the "zero time" reading. All readings were made at room temperature (18.5° C). To determine the activity present on the solid-phase enzyme preparations, five stirred solutions containing ABTS reagent (2.5cm³) and substrate solution (500μl) were treated at room temperature and at one minute intervals, with an aliquot (25μl) of uniformly suspended cellulose. The two control samples were suspended in 5.0cm³ of phosphate buffer (0.1M, ph7.0). The test sample was also originally suspended in 5.0cm³ but had to be diluted again (100 x): 50μl of the suspension was diluted to 5.0cm³ with buffer. Aliquots (25μl) for assay were then taken from these more dilute suspensions. At intervals of five minutes aliquots of 500μl were taken from the supernatant of each incubating suspension after rapid centrifugation. Removal of the supernatant from the solid cellulose stopped the reaction: the optical densities of the supernatant were then read at 415nm against buffer (Table 45).

Table 45

Enzymic Activities on the Peroxidase/Cellulose Preparations as Determined on Assaying with hydrogen peroxide and ABTS.

| Sample | Enzymic Activity (Units*/mg** protein) | % Activity** (relative to soluble enzyme) |
|---|---|---|
| Control:cellulose/enzyme | 0.0 | 0.0 |
| Test:cellulose/DAB/enzyme | 0.27 | 17.0 |
| Soluble enzyme | 1.60 | 100.0 |

(*,** defined as previously).

EXAMPLE 21

Chymotrypsin was coupled to the cellulose-diaminobenzene polymer as in Example 7(1) but 0.5cm³ of a 10mg/cm³ solution of chymotrypsin in 0.2M phosphate buffer pH7.0 was added to each of the solids. No further washing was required after the sucrose-salt/buffer series of washes had been carried out. After suspending the solids in phosphate buffer (0.2M, pH7.0, 5.0cm³), the enzymic activity present on the solids was determined.

Determination of Chymotrypsin activity: a variation of the proteinase assay, using casein as substrate, was carried out. Four tubes were prepared as follows:
"Text" cellulose: 1000μl of cellulose-DAB-enzyme suspension.
"Control" cellulose: 1000μl of cellulose-enzyme suspension.
Soluble enzyme: 1000μl enzyme (10 g/cm³ in phosphate buffer, 0.2M, pH7.0).
Reagent blank: 1000μl buffer.

At known times casein (5% w/v in phosphate buffer, pH7.0 - heated at 100° C for eight minutes to denature the protein, then cooled and centrifuged, 200μl) was added to each tube and immediately after agitation an aliquot (0.2cm³) removed from the tube and added to a tube containing trichloroacetic acid (6.5%, 200μl). The TCA-sample containing tube was immediately stirred on a virtex stirrer while the casein-enzyme sample tube was returned to a water bath (37° C) and incubation continued. Aliquots were similarly taken at 5 minute intervals over 25 minutes. When all aliquots had been taken, the TCA-sample tubes were centrifuged for 5 minutes. 200μl Aliquots were then removed from each and transferred to clean tubes. To each of these was added sodium hydroxide (0.5N, 300μl) and the solutions vigorously agitated. Folin and Ciocaltou's Reagent (20μl) was then added to each of the tubes and they were agitated on the vortex stirrer immediately. After ten minutes the optical densities of the solutions were determined at 660nm against a water blank (Table 46).

Table 46

Enzymic Activities on the Chymotrypsin/Cellulose Preparations as Determined on Assaying with Casein.

| Sample | Units of Enzymic Activity Detected | % Activity** (relative to soluble enzyme) |
| --- | --- | --- |
| Control: Cellulose/enzyme | 0.05 | 0 |
| Test: Cellulose/DAB/enzyme | 0.85 | 3.4 |
| Soluble enzyme | 25.50 | 100 |

(**As defined previously.)

EXAMPLE 22

Linkage of Uricase to Cellulose

Diaminobenzene (0.05gm), "Sigmacell" cellulose (0.10gm) and hydrochloric acid (1.0N, 2.0 ml) were combines in a stoppered test-tube. Aqueous sodium nitrite, pre-cooled to 0° C (2% w/v, 2.0 ml). The solid was then washed three times with 5 ml volumes of pre-cooled (0° C), acetate buffer (0.2M, pH5.0) and then two similar washes using pre-cooled boratebuffer (0.1M, pH 8.5) in preparation for addition of the enzyme which is soluble at an alkaline pH only.

An ampoule of uricase (dry solid) containing 75 Practorius units ≡ 0.443 units, (a unit being defined as: that amount of enzyme causing the conversion of 1μmol uric acid to allantoin per minute at 25° C), was dissolved in ice-cold borate buffer (0.1M, pH 8.5) and made up to a total volume of 10 mls, with buffer. An aliquot (1 ml≡0.0443 units) was added to the test and a control sample of cellulose, which had no diaminobenzene added during the above described procedure. The suspensions were stirred overnight (18 hours) at 4° C.

β-Naphthol, (saturated, in saturated aqueous sodium acetate and filtered through a No. 4 sinter - 2.0 mls) was added to each stirred suspension the following morning and stirred at room temperature for 30 minutes. Each sample was centrifuged, the supernatants discarded and the cellulose then washed using five cycles of alternate washes using (a) ice-cold acetate buffer (0.2M, pH 5.0 - 5 mls), and (b) ice-cold 1M sucrose, 1M sodium chloride in acetate buffer (0.2M, pH 5.0). This was followed by three washes using the buffer as in (a) and three washes with borate buffer (0.1m, pH 8.5 - 5 mls). The cellulose was suspended in a total volume of 2 mls and an aliquot of 1 ml was removed from each tube for assay for uricase activity.

Assay for Uricase 0.1M borate buffer pH 8.5

Subatrate — 10 mg uric acid dissolved in 25 ml buffer and diluted (200 ul → 10 mls) with buffer to give an extinction of 0.550 at 293 mμ.

Enzyme — for standard.

An aliquot of 50 μl was diluted to 250μl with borate buffer (0.1M, pH 8.5) taken from the stock solution (10 mls ≡ 0.443 units). Thus, the standard aliquot was ≡ 0.002215 units.

Procedure

Substrate and enzyme solutions at 25° C i. Standard

Substrate solution (1 ml) was added to enzyme ≡ 0.002215 units (250μl) at zero time. After rapid, thorough mixing on a vortex stirrer, an aliquot was placed in a micro cell and the decrease of extinction at 293 mμ was recorded at minute intervals for 30 minutes.

ii Test and Control Cellulose Suspensions

Substrate solution (1 ml) was added to each of four identical aliquots (250 μl) stirring in conical centrifuge tubes at 25° C, at intervals of 10 minutes. Thus the longest incubation time would be 30 minutes; the rest 20, 10 and (the nearest possible to) a zero time. On addition of the final substrate aliquot to the fourth stirred suspension the tubes were rapidly transferred to a centrifuge and centrifuged, initially for 1 minute, the supernatant of each solution being removed and placed in another tube for recording the OD at 293 mμ. It was found that more thorough centrifugation was necessary to completely remove any tiny particles of suspended cellulose which gave very high false readings. Repeated centrifugation of the supernatants, was carried out until the "zero" time sample gave the reading given by the substrate (diluted in the same proportion with borate buffer (0.1M, pH 8.5), as the cellulose suspension and substrate,) or until the reading was constant after several centrifugations.

The test and the control suspensions were assayed in separate batches to ensure that there would be no time delay in establishing the "zero" time at the centrifugation stage when the reaction is stopped by immediate contrifugation and removal of the supernatant.

All readings were plotted. A first order plot was made for both the standard (at times of 5 minute intervals only) and the cellulose test and control. The number of units of uricase activity on the test cellulose were calculated by comparison of the rates of decrease of OD at 293 mμ between the standard and test cellulose. The % activity coupled was 17.75% of the activity applied to the cellulose.

| Enzyme/Sample | Mgs of Enzyme Offered to 100 mgs of Cellulose | Volume Assayed (cm$^3$) | Uptake of NaOH at five/ Minute | Units of Enzymic Activity Detected | % Enzyme Activity Detected |
|---|---|---|---|---|---|
| Papain | | | | | |
| "test" (1.0 mg/cm$^3$) | 5.0 | 0.1 | 0.0083 | 6.25 | 35 |
| "control" (1.0 mg/cm$^3$) | 5.0 | 0.1 | 0.000 | 0.00 | 0 |
| "soluble" (1.0 mg/cm$^3$) | | 0.1 | 0.0248 | 17.81 | 100 |

EXAMPLE 23

Linkage of Papain to Cellulose

Diaminobenzene (50mgs), 'Sigmacell' cellulose (100 mgs) and hydrochloric acid (1.0N, - 2.0 mls) were combined in a stoppered test tube. Pre-cooled (0° C), aqueous sodium nitrite (2% w/v, 2.0 mls) was added and the suspension stirred at 0° C for 30 minutes. The solid was then washed three times with phosphate buffer (0.1M,pH 7.0 - 5 mls) also pre-cooled in ice-water, and the supernatant from the final wash was then removed.

Papain obtained as a suspension in 0.05M acetate buffer was centrifuged, the supernatant discarded and the white crystalline solid (25 mgs) was diluted with an activating buffer (0.1M phosphate, 0.005M crysteine hydrochloride, 0.002M ethylenediaminetetraacetic acid,pH 7.0) to give an enzyme concentration of 5 mg/ml. The cellulose was treated with papain (5 mgs) and stirred at 0° C for 30 minutes. A control cellulose was prepared following the above procedure but omitting the diaminobenzene. β— Naphthol (saturated, in saturated sodium acetate — 2 mls) was added to each tube and the suspensions were stirred overnight (16 hours) at 4° C. The solids were then subjected to five cycles of alternate washes with the following ice-cold buffers:

a. 0.1M phosphate buffer pH 7.0, containing 0.005M cysteine hydrochloric and 0.002M ethylenediaminotetraacetic acid (E.D.T.A.) — (5 mls)
b. 1M sucrose with 1M sodium chloride in the above activating buffer (a) -(5 mls).

Finally the cellulose was washed five times with a solution of 0.001M cysteine hydrochloride, and 0.0004M E.D.T.A. in water, adjusted to pH 6.5 with 1N NaOH. Thus cellulose was suspended in a final volume of 5 mls.

Determination of Papain Activity

A potentiometric determination of the acid produced during the hydrolysis of benzoyl arginine ethyl ester was carried out using an automatic titrator.

The test system was set up as follows, at 25°: activating diluent (0.001 M cysteine hydrochloride, in 0.004M E.D.T.A. in water adjusted to pH 6.5 with 1N NaOH; 1.0 cm$^3$), substrate (0.05 M benzoyl arginine ethyl ester in activating diluent; 0.50 cm$^3$) and enzyme sample (100 mg cellulose previously treated with 5 mg enzyme, and suspended in 5.0 cm$^3$ of activating diluent: 0.10 cm$^3$) were combined. The number of millilitres of 0.015 N NaOH recuired to maintain the pH at 6.5 after addition of the enzyme was automatically recorded, during a five minute period (one unit of activity is defined as the amount of NaOH required per minute to maintain the pH at 6.5)

EXAMPLE 24

Removal of Protein from Solid-Phase Enzyme Preparations by Treatment with Sodium Dithionite 0.5 cm$^3$ aliquots of the β-glucosidese/cellulose preparation (Example 3, method c) and of the dextranase/cellulose preparation (Example 5, a) were taken, centrifuged and the supenatants discarded. To the solids were added an aqueous solution of sodium bicarbonate (0.1M; 1.0 cm$^3$) and the suspensions were allowed to stir at room temperature. Sodium dithionite (0.035 gms dissolved in 1.0 cm$^3$ sodium bicarbonate solution) was then added to each suspension and stirring continued for five hours at room temperature. The colours of the solid cellulose/enzyme complex was observed to become gradually lighter, changing from dard-red to orange in colour. This was not observed with control samples being treated simultaneously and in exactly the same way but with the omission of dithionite from the reaction mixtures.

When treatment with dithionite was completed the suspensions were centrifuged and the supernatants removed to dialysis tubing, prior to being dialysed overnight against acetate buffer (0.2M, pH 5.0). The solids were washed overnight with acetate buffer.

Treatment with sodium dithionite, a powerful reducing agent, is thought to reduce te diazo links between the diaminobenzene and tyrosine residues on the protein molecules, allowing free diaminobenzene and protein molecules to 'float off' the solid into solution. Studies of dithionite-treated β-glucosidase have shown that this treatment does not appear to affect the activity of the enzyme significantly. When the enzymic activities of the solids and supernatants recovered after treatment of solid phase β glucosidase/cellulose preparations with dithionite were determined, results obtained indicated that much of the protein removed from the solid remained enzymically active.

Table 47

Enzymic Activity Remaining on Solid and Supernatant samples after Treatment of β-Glucosidase Preparations with Sodium Dithionite.

| Treatment | Activity on Solid | Activity in Supernatant |
|---|---|---|
| Sodium bicarbonate | 18.2% | 0 |
| Sodium bicarbonate/ sodium dithionite | 2.5% | 16.8% |

It would appear that this method will have considerable application and utility in the determination of the amounts of protein coupled ono solid-phases.

EXAMPLE 25

Coupling of Glucamylase to Celite (Mesh 80-120)
Optinisation of pH of coupling of enzyme Diaminobenzene (0.05 gms), celite (0.10 gms), and hydrochloric acid (1.0N - 2.0 mls) were mixed in a stoppered test-tube and pre-cooled to 0° C. Aqueous, sodium nitrite (2% w/v, 2.0 mls at 0° C) was added and the suspension stirred at 0° C for 30 minutes. The solid was then washed three times with an ice-cold acetate buffer (0.2M, pH 4.5 × 5 mls). Eight samples of celite were prepared as described and together with eight control celite samples for which treatment with diaminobenzene was omitted. The prepared solids were then wshed once using the buffer which was to be employed in the enzyme coupling stage; these were as follows:
0.2M acetate buffer pH 3.5
0.2M acetate buffer pH 4.0
0.2M acetate buffer pH 4.5
0.2M acetate buffer H 5.0
0.2M acetate buffer pH 5.5
0.2M acetate buffer pH 6.0
0.2M acetate buffer pH 7.0
0.1M phosphate buffer pH 8.0

The crude glucamylase was dialysed against distilled water for 18 hours at 4° C with stirring. The dialysed enzyme was then assayed using the Lowry assay to determine the total protein concentration, which gave a concentration of 16.2 mg/ml. The solution was then diluted to give a concentration of 16.0 mg/ml. Each pair of test and control celite was treated with glucamylase (4 mg/0.25 ml) suspended in the buffer selected for coupling (1.0 ml) and the suspensions were stirred overnight at 4° c.

β-Naphthol (saturated in saturated sodium acetate - 2 ml) was added to each suspension and stirred at room temperature for 30 minutes. The coupled solids were then washed twice wtih 5 mls of the buffer employed during coupling and then with five cycles of alternate washes using first acetate buffer (0.2M. pH 4.5) and then 1M sucrose, and 1M sodium chloride in the same buffer (pH 4.5) Finally the solids were washed five times with acetate buffer (0.2M, pH 4.5 - 5 mls) and suspended in 5 mls of buffer.

Assay for glucamylase Activity

Substrate —Starch solution, 1% in acetate buffer 0.2M, pH 4.5).
Reagent: 1 ml of O-Dianisidine (10 mg/ml in 95% ethanol) 10 mg of glucose oxidase — 5 mg of peroxidase made up to a total volume (100 ml) with tris-HCl buffer 0.5M, pH 7.0. (The reagent was maintained at 0° C, and kept in the dark prior to incubation).

One tube was prepared for each celite test and control, and for a blank and glucamylase standard. Aliouots (100μl) of celite suspension, acetate buffer (0.2M, pH 4.59 or glucamylase (0.16 mg/ml) were taken into tubes. At zero time substrate (1.0 ml) was added to a tube, stirring at 37° C, and a sample of the mixture (50μl) was removed and mixed with reagent (1.5 ml) pre-cooled and stored at 0° C away from the light. Aliquots were removed from each tube at intervals of 7 minutes for 21 minutes. When all aliquots had been collected and mixed with reagent the celite suspensions were rapidly centrifuged and the supernatant removed from the solid prior to incubation. (This was a precaution taken to prevent absorption of colour (produced during incubation of the sample with the reagent) onto the celite). Each tube was then sealed with 'para film' and samples were incubated at 37° C for 1 hour. The tubes were then cooled, thoroughly mixed and the optical desnities of the solutions determined at 450 mm.

Results

All celite control samples gave almost identical readings, all indicating no activity. Reading made at 450 μ against distilled water.

| Tube | Zero | 7 | 14 | 21 minutes |
| --- | --- | --- | --- | --- |
| Blank | 0.056 | 0.059 | 0.061 | 0.057 |
| Celite controls | 0.037 | 0.039 | 0.044 | 0.041 |
| Celite test pH 3.5 | 0.057 | 0.400 | 0.765 | 1.233 |
| Celite test pH 4.0 | 0.062 | 0.568 | 1.261 | 1.695 |
| Celite test pH 4.5 | 0.063 | 0.471 | 0.990 | 1.436 |
| Celite test pH 5.0 | 0.074 | 0.444 | 0.935 | 1.426 |
| Celite test pH 5.5 | 0.032 | 0.453 | 0.962 | 1.420 |
| Celite test pH 6.0 | 0.077 | 0.450 | 0.990 | 1.361 |
| Celite test pH 7.0 | 0.072 | 0.550 | 1.105 | 1.565 |
| Celite test pH 8.0 | 0.078 | 0.355 | 0.648 | 0.964 |
| Standard glucamylase 160 μg/ml | 0.078 | 0.360 | 0.652 | 0.965 |

Comparing the increase in optical density from zero to 14 minutes between the celite and standard samples the results show that the %'s of glucamylase activity on the solids to that applied to the solids in solution are as follows:

| | % activity |
| --- | --- |
| Celite pH 3.5 | 24.6 |
| Celite pH 4.0 | 41.7 |
| Celite pH 4.5 | 32.3 |
| Celite pH 5.0 | 30.0 |
| Celite pH 5.5 | 30.65 |
| Celite pH 6.0 | 31.8 |
| Celite pH 7.0 | 36.0 |
| Celite pH 8.0 | 19.85 |

Thus, the optimum pH of coupling is pH 4.0, pH 7.0 being the second best.

b. Optimasation of proportion of diamino benzene to celite

The coupling of glucamylase to celite was again carried out as previously described (see (a)), at pH 4.0 with the following modifications. Five separate samples of celite (0.10 gms) were placed in stoppered test tubes with varying quantities of diaminobenzene and quantities of sodium nitrite and 1N Hydrochloric acid:

| | Diaminobenzene | 2% sodium nitrate | 1N. HCl |
| --- | --- | --- | --- |
| (a) | 10 mg | 2 ml | 2 ml |
| (b) | 25 mg | 2 ml | 2 ml |
| (c) | 50 mg | 2 ml | 2 ml |
| (d) | 75 mg | 3 ml | 3 ml |
| (e) | 100 mg | 4 ml | 4 ml |
| (f) | 200 mg | 8 ml | 8 ml |

The coupling and subsequent treatment with 62 -naphthol and cycles of washing with buffers at pH 4.5 were carried out as described in the previous experiment with one exception. Where quantities of diaminobenzene exceeded b=mgs it was very difficult to see marked improvement in removal of colour from the supernatants even in the actate buffer (0.2M, pH 4.5) washes. Finally, the samples with 100 and 200 mgs of diaminobenzene were abandoned and the 75 mg one was washed using at least double the usual number of alternate buffer and sucrose, sodium chloride buffer wshes before the supernatant was reasonably pale in colour. Where quantities of D.A.B. were less than 50 mg washing was very easy. After washing several times in acetate buffer (0.2M, pH 4.5) the celite samples and thecontrol celite were suspended in acetate buffer (0.2M, ph 4.5 - 10 mls).

Assay for Glucamylase Activity

Assay was carried out on each sample, a blank and standard exactly as described in (a). Optical densities of supernatants/solutions after sampling incubaing glucamylase preparations with starch at 7 minutes intervals at 37° C, followed by addition of 50μ1aliquots to 1.5 ml of o-dianisidine reagent and further incubation at 37° C for 1 hour, were read against watar 450 mμ.

| Readings DAB. | Tube | Zero | 7 | 14 | 21 min. |
|---|---|---|---|---|---|
| | Blank | 0.056 | 0.059 | 0.061 | 0.057 |
| | Control Celite | 0.037 | 0.039 | 0.044 | 0.041 |
| 10 mg | Test Celite | 0.045 | 0.066 | 0.097 | 0.119 |
| 25 mg | Test Celite | 0.054 | 0.142 | 0.230 | 0.307 |
| 50 mg | Test Celite | 0.053 | 0.311 | 0.600 | 0.920 |
| 75 mg | Test Celite | 0.055 | 0.309 | 0.598 | 0.922 |
| Standard glucamylase | | 0.078 | 0.360 | 0.653 | 0.965 |

($\equiv$ 160 μg/ml.)

Comparison of the increase in optical densities of the celite preparations, from zero to 14 minutes, with the increase in the standard enzyme show the %'s of glucamylase activity on the solids to that applied to the solids in solution are as follows:

| | % activity |
|---|---|
| Celite (100 mg) + DAB (10 mg) | 3.62 |
| Celite (100 mg) + DAB (25 mg) | 12.25 |
| Celite (100 mg) + DAB (50 mg) | 38.20 |
| Celite (100 mg) + DAB (75 mg) | 37.80 |

EXAMPLE 26

Large Scale Preparation of Glucamylase Insolubized on Celite

Diaminobenzene (25.0 gms), celite (50.0 gms) and hydrochloric acid (1.0 N; 1.0 litre) were combined and cooled to 0 in a large beaker. Pre-cooled (0°) aqueous sodium nitrite (2% w/v; 1.0 litre) was slowly added and the suspension stirred at 0° for forty-five minutes. The solid was then washed with a total volume of eight litres of ice cold acetate buffer (0.2 M, pH 4.5), using a No. 4 glass sinter and a suction pump to recover the solid from suspension. When washing was completed the celite was transferred to a beaker containing glucoamylase (5.0 gms total protein/liter in acetate buffer, 0.2 M, ph 4.0; 0.5 liter). The suspension was stirred at 4 for eighteen hours.

Annealing with β-naphthol (saturated, in saturated sodium acetate; 1.0 liter) was allowed to proceed for four hours. The solid was then packed into a chromatography column and washed continuously overnight with acetate buffer (0.2 , pH 4.5). The solid was then subjected to washing with acetate buffer (0.2 M, pH 4.5; 10.0 liters), sucrose-salt/buffer solution (1 M in sodium chloride and 1 M in sucrose, in 0.2 M acetate buffer, pH 4.5; 8.0 liters), and finally acetate buffer again (0.2 M, pH 4.5; 10.0 liters), using a glass sinter as before.

The insolubilized glucamylase was suspended in acetate buffer (0.2 M, ph 4.5; 0.5 liters). An aliquot (1.0 cm³) of the suspension was taken and subjected to a series of washings, first with distilled water (5 × 3.0 cm³) to remove buffer salts, then with ethanol (5 × 3.0 cm³) and finally with ether (5 × 3.0 cm³). Removal of the ether was effected by gentle warming on a water bath. The partially dried solid was then stored in a vacumm desiccator for four hours, before transferred to a chloroform drier for eighteen hours. The weight of the washed and dried solid was then determined: from this total yield of insolubilized enzyme was found to be 42.6 gms of solid.

Another aliquot (0.1 cm³) of the suspension was taken for assay for enzymic activity. Results are reported in Table 48.

Table 48

| Enzymic Activity Detected on Insolubilized Glucoamylase Prepared on a Large Scale for Column Use | |
|---|---|
| Weight of insolubilized enzyme prepared: | 42.6 gms |
| Weight of insolubilized enzyme assayed: | 0.652 mgs |
| Change in Optical Density per minute: | 0.0056 |
| Units of Enzymic Activity on Sample assayed: | 0.0225 units |
| Units of Activity per Gram of insolubilised enzyme: | 34.6 units |
| Total units of activity on insolubilised enzyme: | 34.6 × 42.6 = 1472units |
| Units of Enzymic Activity per Gram of Soluble enzyme: | 5843.75 units |
| Units of Enzymic Activity to the Solid: | 2.5 × 5843.75 = 14,580 units |
| % Enzymic Activity Retained and Detected after Insolubilization: $\frac{1472}{14,580} \times 100 = 10.1\%$ | |

EXAMPLE 27

Use of Insolubilized Glucoamylase/Diaminobenzene/Celite in Column Form for Conversion of Maltose to Glucose A column approximately 36 cms long and 2.5 cms in diameter was packed with approximately 39.7 gms of the insolubilized preparation of glucoamylase (prepared as described in Expt. 31; activity = 34.6 units/gm).

The column was equilibrated with acetate buffer (0.05 M, pH 4.5). Maltose was then continuously passed down the column for seventy-five hours. The maltose solution (2% w/v in acetate buffer, 0.05 M, pH 4.5) was prepared before commencement of the experiment and stored in two dark Winchester bottles, previously thoroughly cleaned and sterilized, to which chloroform (5.0 cm³) had been added to help prevent the growth of bacteria. Samples of the maltose solutions were taken for assay at regular intervals to ensure that observed conversion to glucose after passage through the column was not due to decomposition of maltose in the reservoir bottles.

Samples of the column effluent were taken at half-hourly or hourly intervals. Flow-rate and temperature were recorded at the same time. The column was left 'running' overnight, a sample of the total overnight eluate being taken for assay the next morning.

The glucose contents of the fractions taken were determined on suitably diluted aliquots of the column effluent using the A.B.T.S. method of assay. An aliquot (0.2 cm³) of diluted column effluent was taken onto a test tube and cooled on ice. Ice cold A.B.T.S. reagent (2.5 cm$^3$) was then added to the tube, which was transferred at known time to a waterbath for incubation at 37° for fifteen minutes. Optical densities after incubation were determined at 415 nm against a water blank. Results are given in Table 49.

mg)/cellulose (100 mg) were therefore prepared in weighed test tubes following the usual method. The solids were freeze-dried overnight and weighed: weights of the products were found to be 142.2 mg, 144.8 mg, 146.7 mg and 149.4 mg. Using the average value of 145.8 mg the total weights of protein insolubilized could be calculated. Results are reported in Table 50.

Table 50

Determination of the Bound Protein in the Insolubilised β-Glucosidase Samples Prepared By Offering Different Quantities of Enzyme to Diazotized Diaminobenzene/Cellulose, Using a Paper Chromatographic Method

| Amount of Enzyme Offered to 100 mg Cellulose (mgs) | Optical Density of Extracted material (575 nn)$^a$ | Mg of enzyme Coupled | %Activity Detected Assuming All Offered To have Coupled | % Enzyme Coupled | %Efficiency $= \frac{\%\text{Activity}}{\%\text{Coupled}} \times 100$ |
|---|---|---|---|---|---|
| 1.0 | 0.077 | 0.96 | 103 | 96 | 135 |
| 3.0 | 0.162 | 1.94 | 74 | 65 | 114 |
| 4.0 | 0.223 | 2.69 | 69 | 62 | 111 |
| 5.0 | 0.230 | 2.62 | 56 | 56 | 100 |
| 8.0 | 0.263 | 3.24 | 36 | 41 | 88 |
| 10.0 | 0.315 | 3.89 | 25 | 39 | 64 |

$^a$These Figures were related to the calibration graph, enabling determination of the amount of enzyme coupled to a Solution of Maltose Through a Column of Insolubilised Glucoaylase Continuously for Seventy five Hours.

| Tube No. | Time (hr) | Temp (° C) | Flow Rate (mls per min) | Contact time* (mins) | Optical Density (minus blank) | %Conversion to Glucose | %Conversion contact time |
|---|---|---|---|---|---|---|---|
| 0 | 0.0 | 23.0 | 1.33 | 120 | 0.000 | 0.0 | 0.0 |
| 5 | 2.0 | 23.0 | 1.33 | 120 | 0.450 | 63.6 | 0.58 |
| 10 | 4.5 | 23.0 | 1.33 | 120 | 0.494 | 70.2 | 0.58 |
| 15 | 21.0 | 22.8 | 0.43 | 395 | 0.547 | 77.3 | 0.20 |
| 20 | 23.5 | 23.8 | 0.43 | 395 | 0.504 | 71.0 | 0.18 |
| 25 | 26.0 | 24.0 | 0.40 | 400 | 0.544 | 76.8 | 0.19 |
| 30 | 28.5 | 22.8 | 0.44 | 394 | 0.528 | 74.6 | 0.19 |
| 35 | 49.0 | 24.1 | 0.29 | 551 | 0.441 | 63.0 | 0.11 |
| 40 | 53.0 | 22.2 | 0.29 | 551 | 0.498 | 71.4 | 0.13 |
| 45 | 75.0 | 22.4 | 0.23 | 696 | 0.507 | 73.5 | 0.11 |
| 48 | 75.0 | 22.6 | 0.23 | 696 | 0.573 | 82.8 | 0.12 |

* The contact time is the time for which the liquid in flowing through the column, i.e.

$$\text{Contact time} = \frac{\text{Packed Column Volume (cm}^3\text{)}}{\text{Flow Rate (mls/min)}} = \frac{159.5 \text{ cm}^3}{\text{Flow Rate}}$$

EXAMPLE 28

Determination of the Weight of β-Glucosidase Insolubilized onto Cellulose Using a Quantitative Paper Chromatographic Method Six samples of insolubilized β-glucosidase previously prepared were taken for determination of the weight of protein insolubilized. After removal of an aliquot (1.0 cm$^3$) of each suspenson of use in a subsequent experiment, the remainder of each solid was washed several times with water to remove buffer salts, and the solids were then freeze-dried overnight. Samples (50 mgs) of each dried solid were then weighed into separate hydrolysis tubes and suspended in hydrochloric acid (6.0 M; 1.0 cm$^3$). Crystalline ("soluble") β-glucosidase (5.0 mg) was weighed into a hydrolysis tube containing cellulose (100 mg), and similarly treated with acid. A standard hydrolysis procedure was then followed (see below).

Paper chromatographic analysis of each of the hydrolysates was then carried out. By using the calibration graph the quantity of β-glucosidase present in each hydrolysate could be determined.

In order to calculate the total weight of enzyme insolubilized it was necessary to known the total dry weight of the diaminobenzene/cellulose complex after freezedrying. Four fresh samples of diaminobenzene (50

Determination of Protein Content by the Chromatographic Method of Kay, Harris and Entenman The dried and neutralized residues from the hydrolyses were dissolved in the chromatography solvent (water/n-butanol/acetic acid (5/4/1) mixture): residues from the soluble enzymes were taken up in 1.0 cm$^3$, and the insolubilized enzyme residues were dissolved in 0.2 cm$^3$.

Aliquots (0.010 cm$^3$) of each solution to be estimated were applied as small spots at intervals of one inch along the origin of the chromatogram (Whatman No. 1 Paper). Standard solutions of each soluble enzyme were applied after preparing successive double dilutions of the 5 mg/cm$^3$ enzyme standard. Descending chromatography was carried out over 20 hours using the upper layer of the solvent mixture, the paper first having been equilibrated in the solvent vapour for 2 hours. The paper was air dried, and then sprayed as evenly as possible, until translucent, the ninhydrin reagent (0.5 g ninhydrin, dissolved in 100 cm$^3$ ethanol/water (3:1 v/v) containing 0.5 cm$^3$ of 1 M sodium hydroxide solution). The paper was developed in a hot air oven at 65° for 22 minutes.

The most clearly defined of the ninhydrin positive amino acid spots, common to both the standard and insoluble enzyme samples, was chosen and cut from the paper. The same section of the paper (approximately 1 cm × 1 cm) was similarly cut for each of the samples applied to the paper. Each piece of paper was put into a separate assay tube and the chromophore extracted with 1.0 cm$^3$ of ethanol/water (3:1 v/v). The extraction was allowed to proceed, with occasional gentle shaking, for two hours at room temperature. A piece of the chromatogram containing no ninhydrin positive material was treated in the same way and used as a blank. The optical densities of the solutions obtained from elution of each spot were measured at 575 nm. From the readings obtained, calibration graphs were plotted for each enzyme, and the amount of protein present in each of the original insolubilized enzyme samples thus determined.

EXAMPLE 29

Determination of the weight of glucose oxidase, peroxidase, catalase and uricase insolubilized onto cellulose, using a quantitative paper chromatographic method Samples of each of the insolubilized enzymes (50 mgs) prepared as previously described were weighed into separate hydrolysis tubes and the procedure described above again followed.

Results of these protein determinations are given in Table 51.

Table 51

Determination of the bound protein in insolubilized samples of glucose oxidase, peroxidase, catalase and uricase using a paper chromatographic method

| Amount of enzyme offered to 100 mg cellulose (mgs) | Optical density of extracted material (575 nm)[a] | Mg of enzyme coupled[b] | %Activity detected assuming all offered to have coupled | % enzyme coupled | % efficiency $= \frac{\% \text{ activity}}{\% \text{ coupled}} \times 100$ |
|---|---|---|---|---|---|
| Glucose oxidase 5.0 | 0.136 | 0.74 | 27.3 | 29 | 93.0 |
| Peroxidase 5.0 | 0.062 | 0.53 | 14.1 | 22 | 66.3 |
| Catalase 5.0 | 0.186 | 1.13 | 31.4 | 45 | 69.5 |
| Uricase (0.0886 units) | 0.043 | (0.0620 units) | 21.8 | 70 | 31.2 |

[a]By relating these figures to the calibration graphs previously prepared the amount of each enzyme which had coupled could be determined.
[b]These represent the wts couples per 50 mg of insolubilized preparation.

EXAMPLE 30

Freeze-drying of Insolubilized β-glucosidase

Six aliquots (1.0 cm³ each) of the β-glucosidase sample (prepared by the method of Example 3(b) doubling all reagent quantities) were taken into six tubes. These were centrifuged and the supernatants removed. An aliquot of acetate buffer (0.2 M, pH 5.0; 1.0 cm³) containing sorbitol (5 mg, 10 mg, 25 mg, 50 mg or 100 mg) was added to each. To the sixth tube was added the same volume of buffer but no sorbitol. The tubes were left on a freeze-drier overnight. Drying was incomplete for the two preparations with the highest concentrations or sorbitol, but the other products were dry powders. Each solid was washed three times with acetate buffer (0.2 M, pH 5.0; 1.0 cm³) and then suspended in the same buffer (1.0 cm³) prior to assay of enzymic activity in the usual way. Results are reported in Table 52.

Table 52

Enzymic Activities Detected on Aliquots of Insolubilized β-Glucosidase Freeze-Dried in the Presence of Varying Amounts of Sorbitol

| Weight of Sorbitol (mgs) Added to the Enzyme Conjugate (20 mg cellulose) Prior to Freeze-drying | Change in Optical Density per Minute (Assaying 0.02 cm Aliquots). | % Original Enzymic Activity Retained on freeze-drying |
|---|---|---|
| 0.0 | 0.0394 | 50.5 |
| 5.0 | 0.058 | 74.4 |
| 10.0 | 0.058 | 74.4 |
| 25.0 | 0.062 | 79.5 |
| 50.0 | 0.070 | 90.2 |
| 100.0 | 0.074 | 95.0 |
| Activity of non-freeze-dried Sample | 0.078 | — |

EXAMPLE 31

Freeze-drying of Insolubilized Glucose Oxidase, Peroxidase, Catalase and Uricase An aliquot (1.0 cm³) of each of the insolubilized enzyme suspensions, prepared as previously described, was added to an aliquot of aqueous sorbitol (10% w/v; 1.0 cm³). The suspensions were freeze-dried overnight, and the "sticky" solids remaining were then washed repeatedly with acetate buffer (0.2 M, pH 5.0; 5 × 10 cm³) to remove the sorbitol. The freeze-dried enzymes were then resuspended in buffer (1.0 cm³) using volumetric flasks. The enzymic activity of each of the solids was then determined in the usual way. Results are reported in Table 53.

Table 53

Enzymic Activities Detected on Aliquots of Insolubilized Glucose Oxidase, Peroxidase, Catalase and Uricase Before and after Freeze-Drying in the Presence of Soribitol

| Enzyme | % Enzymic Activity Detected Initially | % Enzymic Activity After Freeze-drying | % Original Activity Retained on Freeze-drying |
|---|---|---|---|
| Glucose Oxidase | 27.30 | 20.35 | 74.5 |
| Peroxidase | 14.14 | 13.12 | 92.9 |
| Catalase | 31.43 | 31.43 | 100.0 |
| Uricase | 21.85 | 17.90 | 81.9 |

EXAMPLE 32 pH-Activity Profiles for Insolubilized and Free β-Glucosidase

The activities of a freshly-prepared sample of water-insoluble β-glucosidase derivative and of the enzyme in solution were determined in the following (0.2 M) buffers: citrate-phosphate pH 2.5; citrate pH 3.0, 3.5, 4.0, 4.5, 5.0, 5.5 and 6.0; phosphate pH 6.5, 7.5, 8.0 and 8.5.

An aliquot (0.5 cm³) of a suspension of the water-insoluble preparation (2.0 mg of solid) in the appropriate buffer was taken for assay. Substrate (0.5 cm³) was added to each tube and the reaction mixtures incubated with stirring for thirty minutes at 37°. An aliquot (0.5 cm³) was then removed and added to sodium carbonate solution (0.2 M; 0.5 cm³). After centrifuging, the optical densities of the supernatants were determined at 420 nm.

A solution of β-glucosidase (2.5 μ/cm³ in the appropriate buffer: 0.5 cm³) was assayed in the same manner.

The activity at each pH value was expressed as a percentage of that at the pH of maximum activity, i.e. pH 5.5 in each case. Results are given in Table 54.

Table 54

Enzymic Activities Detected on Soluble and Insoluble Samples of β-Glucosidase Assayed at Different pH's. Ensymic Activities Expressed as Percentages of that at the pH of Maximum Activity

| pH of Assay Solution | Insoluble | Soluble |
|---|---|---|
| 2.5 | 7.9 | 2.3 |
| 3.0 | 10.9 | 4.0 |
| 3.5 | 26.6 | 16.6 |
| 4.0 | 49.0 | 41.9 |
| 4.5 | 74.5 | 71.7 |
| 5.0 | 90.7 | 96.2 |
| 5.5 | 100.0 | 100.0 |
| 6.0 | 92.2 | 82.4 |
| 6.5 | 78.0 | 61.4 |
| 7.0 | 64.9 | 47.5 |
| 7.5 | 49.7 | 37.4 |
| 8.0 | 37.2 | 24.0 |
| 8.5 | 30.9 | 12.8 |

EXAMPLE 33 pH-Activity Profiles for Insolubilized and Free Dextranase

The activities of a freshly-prepared sample of water-insoluble dextranase derivative (prepared using 5 mg of enzyme) and of the enzyme in solution were determined in the same buffers as used in Example 32.

An aliquot (1.0 cm³) of a suspension of the water-insoluble derivative (20 mg) in the appropriate buffer was taken for assay using a modified version of the usual method. Dextran (1% in water; 2.5 cm³) was added to each tube and the reaction mixtures incubated with stirring for 15 minutes at 37°. Aliquots (0.5 cm³) were then removed to tubes containing DNS reagent (0.5 cm³). After centrifuging and heating the tubes at 100° for 10 minutes, optical densities were determined at 520 nm.

A solution of dextranase (0.2 mg/cm³ in the appropriate buffer) was assayed in the same manner.

The activity at each pH value was again expressed as a percentage of that at the pH of maximum activity, i.e. pH 5.0 for the insoluble enzyme and pH 5.5 for the soluble enzyme. Results are given in Table 53.

Table 55

Enzymic Activities Detected on Soluble and Insoluble Samples of Dextranase Assayed at Different pH's. Enzymic Activities Expressed as Percentages of the Activity at the pH of Maximum Activity

| pH of Assay Solution | Insoluble | Soluble |
|---|---|---|
| 2.5 | 79.2 | 41.4 |
| 3.0 | 55.4 | 44.2 |
| 3.5 | 86.5 | 55.5 |

Table 55-continued

Enzymic Activities Detected on Soluble and Insoluble Samples of Dextranase Assayed at Different pH's. Enzymic Activities Expressed as Percentages of the Activity at the pH of Maximum Activity

| pH of Assay Solution | Insoluble | Soluble |
|---|---|---|
| 4.0 | 95.6 | 53.6 |
| 4.5 | 97.6 | 72.4 |
| 5.0 | 100.0 | 98.2 |
| 5.5 | 71.5 | 100.0 |
| 6.0 | 47.4 | 50.0 |
| 6.5 | 27.2 | 34.4 |
| 7.0 | 13.5 | 12.4 |
| 7.5 | 8.1 | 3.8 |
| 8.0 | — | 2.4 |
| 8.5 | 8.7 | 2.3 |

EXAMPLE 34 pH-Activity Profiles for Insolubilized and Free Glucose Oxidase

The activities of a sample of insolubilized glucose oxidase and of the enzyme in solution were determined at six different pH's: 3.5, 4.5, 5.5, 6.0, 7.0 and 8.0. The usual assay procedure was followed, with minor modification. A.B.T.S. reagent (2.5 cm³), glucose solution (0.5 cm³) and peroxidase solution (0.2 cm³) were combined in one tube for each pH and the tubes were placed in a water bath at 37°. At two minute intervals an aliquot of enzyme solution (0.1 cm³ of a 10 μg/cm³ solution) or of the insolubilized enzyme suspension (0.1 cm³ of a suspenson of 80 μg cellulose/cm³) was added to each tube. Incubation was allowed to proceed at 37° for 10 minutes for each tube. Optical densities of the supernatants were then determined at 415 nm.

The activity at each pH value was expressed as a percentage of that at the pH of maximum activity, i.e. pH 5.5 for both soluble and insolubilized forms of the enzyme. The results are presented in Table 56.

Table 56

Enzymic Activities Detected on Soluble and Insoluble Samples of Glucose Oxidase Assayed at Different pH's. Enzymic Activities Expressed as Percentages of the Activity at the pH of Maximum Activity

| pH of Assay Solution | Insoluble | Soluble |
|---|---|---|
| 3.5 | 28.0 | 47.8 |
| 4.5 | 83.0 | 81.3 |
| 5.5 | 100.0 | 100.0 |
| 6.0 | 92.7 | 88.0 |
| 7.0 | 68.7 | 59.1 |
| 8.0 | 26.5 | 18.8 |

EXAMPLE 35 pH-Activity Profiles for Insolubilized and Free Peroxidase

The activities of a sample of insolubilized peroxidase and of the enzyme in solution were determined at 6 different pH's: 3.0, 4.0, 5.0, 6.0, 7.0 and 8.0. The usual assay procedure was followed, with minor modification. A.B.T.S. reagent (2.5 cm³), glucose oxidase solution (0.1 cm³) and glucose solution (0.5 cm³) were mixed in one tube for each pH and the tubes incubated in a waterbath at 37°. At intervals of three minutes an aliquot of soluble peroxidase solution (0.2 g/cm³; 0.2 cm³) or of a diluted suspension of the insolubilized preparation (theoretically 0.8 g/cm³ peroxidase; 0.2 cm³) was added to each tube. Incubation was allowed to proceed for twenty minutes, after which the optical density of each supernatant was determined at 415 nm after centrifugation.

The activity at each pH value was expressed as a percentage of that at the pH of maximum activity, i.e. pH 5.0 for both soluble and insoluble enzymes. Results are given in Table 57.

Table 57
Enzymic Activities Detected on Soluble and Insoluble Samples of Peroxidase Assayed at Different pH's.
Enzymic Activities Expressed as Percentages of the Activity at the pH of Maximum Activity

| pH of Assay Solution | Insoluble | Soluble |
|---|---|---|
| 3.0 | 14.1 | 0.0 |
| 4.0 | 48.9 | 50.4 |
| 5.0 | 100.0 | 100.0 |
| 6.0 | 57.5 | 41.7 |
| 7.0 | 26.6 | 25.7 |
| 8.0 | 9.7 | 15.1 |

EXAMPLE 36 pH-Activity Profiles for Insolubilized and Free Catalase

The activities of a sample of insolubilized catalase and of the enzyme in solution were determined at six different pH's: 4.0, 5.0, 6.0, 7.0, 8.0 and 9.0. A modified version of the usual assay method was employed to determine the activities for the insolubilized samples. Six stoppered tubes each containing an aliquot (0.4 cm³) of insolubilized enzyme in suspension in the appropriate buffer were treated at three minute intervals with diluted hydrogen peroxide solution (0.2 cm³) in the same buffer. Zero time was recorded on addition of the hydrogen peroxide. After twenty minutes incubation at 25° the absorbances of the solutions after centrifugation were determined at 240 nm. Assays of the soluble enzyme samples were carried out as described.

The activity at each pH value was expressed as a percentage of the activity at the pH of maximum activity, i.e. at pH 8.0 for soluble catalase and at pH 6.0 for the insolubilized preparation. The results are reported in Table 58.

Table 58
Enzymic Activities Detected on Soluble and Insoluble Samples of Catalase Assayed at Different pH's.
Enzymic Activities Expressed as Percentages of the Activity at the pH of Maximum Activity

| pH of Assay Solution | Insoluble | Soluble |
|---|---|---|
| 4.0 | 18.7 | 11.8 |
| 5.0 | 73.7 | 64.0 |
| 6.0 | 100.0 | 73.4 |
| 7.0 | 93.1 | 87.9 |
| 8.0 | 84.9 | 100.0 |
| 9.0 | 69.7 | 67.5 |

EXAMPLE 37 pH-Activity Profiles for Insolubilized and Free Uricase

The activities of a sample of insolubilized uricase and of the enzyme in solution were determined in six borate buffers (0.2 N; pH 7.0, 8.0, 8.5, 9.0, 9.5 and 10.0) The usual assay procedure was followed with minor modification. Substrate solutions (0.5 cm³), prepared using the appropriate buffer, were pipetted into stoppered test tubes containing distilled water (0.5 cm³). The six tubes were placed in a water bath at 37°. At three minute intervals an aliquot of soluble enzyme (0.25 cm³ containing 0.0011075 units) or of insolubilized enzyme suspension (200 mgs cellulose in 10 cm³ water; 0.25 cm³) was added to each tube in turn. After incubating each tube for twenty minutes the optical density of the solutions after centrifuging were determined at 293 nm. Results are reported in Table 59, the activity at each pH value having been calculated as a percentage of that at the pH of maximum activity, i.e. at pH 9.0 for both forms of uricase.

Table 59
Enzymic Activities Detected on Soluble and Insoluble Samples of Uricase Assayed at Different pH's.
Enzymic Activities Expressed as Percentages of the Activity at the pH of Maximum Activity

| pH of Assay Solution | Insoluble | Soluble |
|---|---|---|
| 7.0 | 5.3 | 1.9 |
| 8.0 | 52.7 | 60.0 |
| 8.5 | 67.4 | 65.0 |
| 9.0 | 100.0 | 100.0 |
| 9.5 | 61.0 | 65.5 |
| 10.0 | 26.3 | 1.4 |

EXAMPLE 38

Determination of the Michaelis Constant for c-Nitrophenyl-$\beta$-D-glucopyranoside with Free $\beta$-Glucosidase and Six Insolubilized Enzyme Preparations An aliquot of soluble enzyme (0.005 mg/cm³ in acetate buffer, 0.2 M, pH 5.0; 1.0 cm³) was taken for assay with substrate solution (2.0 mg/cm³ o-nitrophenyl-$\beta$-D-glucopyranoside in acetate buffer; 3.0 cm³) in the usual way. The procedure was repeated using five other solutions of substrate (3.0, 4.0, 6.0, 8.0 and 10.0 mg/cm³).

Aliquots of the six preparations of insolubilized $\beta$-glucosidase earlier described Example 36 were similarly studied: aliquots (0.1 cm³) of diluted suspension (4.0 mg cellulose/cm³) were mixed with acetate buffer buffer (0.2 M, pH 5.0; 0.9 cm³) and assayed with substrate solution of different concentrations as above.

The results of this experiment are reported in Table 60.

Table 60
Determination of the Michaelis Constants ($K_m$) of Six Different Insolubilized Preparations of $\beta$-Glucosidase.

| Mg of Enzyme Insolubilized on 100 mg of Cellulose[a] | % Efficiency[b] | $K_m$ (mole · liter$^{-1}$) |
|---|---|---|
| 0.96 | 135 | $1.557 \times 10^{-2}$ |
| 1.94 | 114 | $1.079 \times 10^{-2}$ |
| 2.69 | 111 | $1.058 \times 10^{-2}$ |
| 2.82 | 100 | $0.587 \times 10^{-2}$ |
| 3.24 | 88 | $1.116 \times 10^{-2}$ |
| 3.89 | 64 | $1.002 \times 10^{-2}$ |

[a]Results as determined in Example 26 and reported in Table 41

[b]% Efficiency = $\frac{\% \text{ Activity}}{\% \text{ Coupled}} \times 100$ (previously defined).

What we claim is:

1. Biologically active material which comprises a water-insoluble solid with a surface to which molecules of diazotized m-diamino-benzene are linked by adsorption, and biologically active protein molecules chemically bonded to said molecules of diazotized m-diamino-benzene.

2. A material as claimed in claim 1 in which said biologically active protein is an enzyme.

3. A material as claimed in claim 1 in which said biologically active protein is a coenzyme.

4. A material as claimed in claim 2 in which said enzyme is selected from the group consisting of glucosidase, dextranase, α-amylase, catalase, glucose oxidase, thermolysin, N-acetyl amino acid amidohydrolase, peroxidase, chymotrypsin, uricase, and papain.

5. A material as claimed in claim 2 in which said enzyme is selected from the group consisting of glucose isomerase, isoamylase, pullulanase, urease, pronase, lactate dehydrogenase and cholin esterase.

6. Material as claimed in claim 1 in which any unreacted diazo groups of said molecules of diazotized m-diamino-benzene have been rendered chemically inert.

7. A material as claimed in claim 1 in which said surface to which said biologically active protein molecules are attached has free hydroxyl groups prior to adsorption thereon of the molecules of diazotized m-diamino-benzene.

8. A material as claimed in claim 1 in which said surface to which said biologically active protein molecules are attached has free polyamide groups prior to adsorption thereon of the molecules of diazotized m-diamino-benzene.

9. A material as claimed in claim 1 in which said solid is selected from the group consisting of silica, nylon, natural cellulose and regenerated cellulose.

10. A material as claimed in claim 1 in which said solid is selected from the group consisting of a diatomaceous earth, polysaccharide, polyamide, polycarbonate, polyester, polyurethane, titanium oxide, zirconium oxide, aluminum oxide, and iron oxide.

11. A material as claimed in claim 1 in which said surface is polar.

12. A packed bed reactor containing a material according to claim 1.

13. A material as claimed in claim 1 in which said water-insoluble solid is a porous molecular sieve.

14. A material as claimed in claim 1 in which said water-insoluble solid is a bead.

15. A material as claimed in claim 1 in which said water-insoluble solid is a tube.

16. A material as claimed in claim 1 in which said water-insoluble solid is a sheet filter.

17. A material as claimed in claim 1 in which said water-insoluble solid is a membrane.

18. A material as claimed in claim 17 wherein the biologically active protein molecules are identical and attached to one or both faces of said membrane.

19. A material as claimed in claim 17 wherein the biologically active protein molecules are different and attached to the same face of the membrane.

20. A material as claimed in claim 17 wherein different biologically active protein molecules are attached to opposite faces of the membrane.

21. A material as claimed in claim 1 in which said solid is selected from the group consisting of crosslinked dextran, polyacrylamide, carboxymethyl cellulose, diethyl amino ethyl cellulose, and cellulose acetate.

22. Biologically active material which comprises a water-insoluble solid, selected from the group consisting of porous glass, porous silica and wood, with a surface to which molecules of diazotized m-diaminobenzene are linked by adsorption, and biologically active protein molecules chemically bonded to said molecules of diazotized m-diamino-benzene.

23. A material as claimed in claim 22 in which said solid is a balsa wood.

24. A method for the preparation of biologically active material, which comprises: chemically bonding biologically active protein molecules to molecules of diazotized m-diamino-benzene linked by adsorption to a surface of a water-insoluble solid.

25. A method as claimed in claim 24 in which said molecules of m-diamino-benzene are diazotized in the presence of said water-insoluble solid.

26. A method as claimed in claim 24 in which said molecules of m-diamino-benzene are diazotized before they are adsorbed on said surface.

27. A method as claimed in claim 24 in which said molecules of m-diamino-benzene are adsorbed on said surface and then said molecules are diazotized.

28. A method as claimed in claim 25 in which any residual diazo groups of said biologically active material are made chemically inert.

29. A method as claimed in claim 28 in which any residual diazo groups are made chemically inert by reacting them with a phenol.

30. A method as claimed in claim 29 in which said phenol is β-naphthol.

31. A method as claimed in claim 24 in which any residual diazo groups are reacted to make said groups chemically inert and to alter the microenvironment of said biologically active protein molecules.

32. A method as claimed in claim 24 in which said surface on which said molecules of diazotized m-diamino-benzene are adsorbed contains free hydroxyl groups prior to adsorbing thereon the molecules of diazotized m-diamino-benzene.

33. A method as claimed in claim 24 in which said surface on which said molecules of diazotized m-diamino-benzene are adsorbed contains free polyamide groups prior to adsorbing thereon the molecules of diazotized m-diamino-benzene.

34. A method for reactivating an inactivated biologically active material comprising a water-insoluble solid with a surface to which molecules of diazotized m-diamino-benzene are linked by adsorption, and inactivated biologically active protein molecules are chemically bonded to said molecules of said diazotized m-diamino-benzene, which comprises:
 a. adsorbing additional molecules of diazotized m-diamino-benzene on said surface; and
 b. attaching fresh biologically active protein molecules to said additional molecules of diazotized m-diamino-benzene.

35. A method for reactivating an inactivated biologically active material comprising water-insoluble solid with a surface to which molecules of a diazotized aromatic diamine are linked by adsorption, and inactivated biologically active protein molecules are chemically bonded to said molecules of said diazotized aromatic diamine, which comprises:
 a. treating said material with sodium dithionite to regenerate amine groups;
 b. diazotizing said amine groups; and
 c. attaching thereto biologically active protein molecules.

36. A method as claimed in claim 35, wherein said diazotized aromatic diamine is diazotized m-diamino-benzene.

* * * * *